US009282922B2

United States Patent
Haar et al.

(10) Patent No.: US 9,282,922 B2
(45) Date of Patent: Mar. 15, 2016

(54) MEDICAL SYSTEM COMPRISING A COMPACT BARCODE READER FOR CONSUMABLE ITEMS

(75) Inventors: Hans-Peter Haar, Wiesloch (DE); Gerrit Kocherscheidt, Heddesheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1304 days.

(21) Appl. No.: 13/021,382

(22) Filed: Feb. 4, 2011

(65) Prior Publication Data

US 2012/0043377 A1    Feb. 23, 2012

Related U.S. Application Data

(63) Continuation of application No. PCT/EP2009/060237, filed on Aug. 6, 2009.

(30) Foreign Application Priority Data

Aug. 6, 2008  (EP) ..................................... 08161928

(51) Int. Cl.
   *A61B 5/145*     (2006.01)
   *A61B 19/00*     (2006.01)
   *A61B 5/1455*    (2006.01)

(52) U.S. Cl.
   CPC ........... *A61B 5/14546* (2013.01); *A61B 5/1455* (2013.01); *A61B 5/14532* (2013.01); *A61B 19/44* (2013.01); *A61B 2019/442* (2013.01); *A61B 2019/446* (2013.01); *A61B 2562/0295* (2013.01); *A61B 2562/08* (2013.01)

(58) Field of Classification Search
   CPC ........... A61B 5/14546; A61B 5/14532; A61B 5/1455; A61B 19/44; A61B 2019/442; A61B 2019/446; A61B 2562/0295; A61B 2562/08
   See application file for complete search history.

(56) References Cited

U.S. PATENT DOCUMENTS

| 4,141,624 | A | * | 2/1979 | Siegmund | G02B 6/065 348/804 |
| 4,476,149 | A | * | 10/1984 | Poppe et al. | 427/2.13 |
| 4,509,859 | A | * | 4/1985 | Markart et al. | 356/446 |

(Continued)

FOREIGN PATENT DOCUMENTS

| JP | 62-97894 A | 5/1987 |
| JP | H05-37718 A | 2/1993 |

(Continued)

OTHER PUBLICATIONS

Lan, J., et al., "Fingerprint Imager Based on a-Si: H Active-Matrix Photo-Diode Arrays", Electric Devices Meeting, 2000.IEDM Technical Digest. International, Dec. 2000, p. 419-422.

*Primary Examiner* — Daniel Walsh
(74) *Attorney, Agent, or Firm* — Quarles & Brady, LLP

(57) ABSTRACT

A medical system is proposed comprising at least one medical device for carrying out at least one medical function, and at least one medical consumable item interacting with the medical device in order to carry out the medical function. The medical device has at least one code reader for reading out at least one information component of an optical code on the medical consumable item. The code reader has at least one image sensor having a plurality of sensors. Furthermore, the code reader comprises at least one light-optical fiber plate, which is arranged in order to guide an image of the optical code to the image sensor.

19 Claims, 8 Drawing Sheets

(56) References Cited

U.S. PATENT DOCUMENTS

| | | | |
|---|---|---|---|
| 4,510,383 A * | 4/1985 | Ruppender | 235/462.21 |
| 5,714,123 A * | 2/1998 | Sohrab | G01N 33/52 422/117 |
| 5,742,718 A * | 4/1998 | Harman et al. | 385/53 |
| 6,168,957 B1 | 1/2001 | Matzinger et al. | |
| 6,588,670 B2 * | 7/2003 | Bukowski | 235/462.45 |
| 6,867,051 B1 * | 3/2005 | Anderson et al. | 436/518 |
| 7,175,091 B2 * | 2/2007 | An | G06K 13/08 235/436 |
| 7,419,098 B2 * | 9/2008 | Hyde et al. | 235/462.43 |
| 8,509,879 B2 * | 8/2013 | Durkin | A61B 5/0073 600/407 |
| 8,608,052 B2 * | 12/2013 | Hensel | G06K 7/10732 235/375 |
| 2002/0147317 A1 * | 10/2002 | Bentsen et al. | 536/8 |
| 2003/0090650 A1 | 5/2003 | Fujieda | |
| 2003/0119207 A1 * | 6/2003 | Dejneka et al. | 436/524 |
| 2004/0082918 A1 | 4/2004 | Evans et al. | |
| 2004/0100570 A1 | 5/2004 | Shizukuishi | |
| 2004/0241752 A1 * | 12/2004 | Anderson et al. | 435/7.1 |
| 2005/0154277 A1 * | 7/2005 | Tang | A61B 1/00016 600/407 |
| 2006/0042633 A1 * | 3/2006 | Bishop et al. | 128/207.18 |
| 2006/0202104 A1 | 9/2006 | Gurevich et al. | |
| 2006/0213994 A1 | 9/2006 | Faiz et al. | |
| 2006/0252088 A1 * | 11/2006 | Dejneka et al. | 435/6 |
| 2007/0030790 A1 * | 2/2007 | Hendriks | G11B 7/0033 369/120 |
| 2007/0167694 A1 * | 7/2007 | Causevic | A61B 5/0402 600/301 |
| 2008/0088731 A1 | 4/2008 | Tanaka et al. | |
| 2008/0145085 A1 * | 6/2008 | Reisinger et al. | 399/68 |
| 2008/0200788 A1 * | 8/2008 | Brister et al. | 600/345 |
| 2009/0157064 A1 * | 6/2009 | Hodel | 606/10 |
| 2009/0204009 A1 * | 8/2009 | Powers | A61B 5/0075 600/476 |
| 2009/0246078 A1 * | 10/2009 | Barnard et al. | 422/56 |
| 2009/0322987 A1 * | 12/2009 | Dunn | G02F 1/133524 349/65 |
| 2010/0022988 A1 | 1/2010 | Wochner et al. | |
| 2011/0039285 A1 * | 2/2011 | Sadaba Champetier De Ribes et al. | 435/13 |
| 2011/0282671 A1 * | 11/2011 | Dicks et al. | 704/270.1 |
| 2011/0301446 A1 * | 12/2011 | Kamen | 600/365 |
| 2012/0043376 A1 * | 2/2012 | Petrich et al. | 235/375 |
| 2012/0043377 A1 * | 2/2012 | Haar et al. | 235/375 |
| 2012/0082598 A1 * | 4/2012 | Baydoun | 422/423 |
| 2012/0211566 A1 * | 8/2012 | Hensel et al. | 235/462.42 |
| 2013/0043310 A1 * | 2/2013 | Petrich et al. | 235/454 |
| 2013/0157381 A1 * | 6/2013 | Pang et al. | 436/501 |
| 2014/0072189 A1 * | 3/2014 | Jena et al. | 382/128 |

FOREIGN PATENT DOCUMENTS

| | | |
|---|---|---|
| JP | H08-212286 A | 8/1996 |
| JP | H10-86563 A | 4/1998 |
| JP | 2003-16198 A | 1/2003 |
| JP | 2003085537 A | 3/2003 |
| JP | 2003-144420 A | 5/2003 |
| JP | 2005-115495 A | 4/2005 |
| JP | 2006-244097 A | 9/2006 |
| JP | 2007-323373 A | 12/2007 |
| KR | 2009046179 A | 5/2009 |
| WO | 2005/027107 A1 | 3/2005 |
| WO | 2006/099317 A2 | 9/2006 |
| WO | 2008/010822 A2 | 1/2008 |
| WO | 2007/128144 A1 | 11/2009 |

* cited by examiner

MEDICAL SYSTEM COMPRISING A COMPACT BARCODE READER FOR CONSUMABLE ITEMS

CLAIM OF PRIORITY

The present application is a continuation application based on and claiming priority to PCT/EP2009/060237, filed Aug. 6, 2009, which itself claims the priority filing benefit of European Application No. 08161928.0, filed Aug. 6, 2008, each of which are hereby incorporated herein by reference in their respective entireties.

TECHNICAL FIELD OF THE INVENTION

The present application relates to a medical system comprising at least one medical device for carrying out a medical function. The medical device is designed to interact with at least one medical consumable item. Medical systems of this type are used, for example, in medical analysis, medical diagnostics or medical therapeutics.

BACKGROUND

The use of medical consumable items is of significant importance in the field of medicine and medical technology. Thus, by way of example, in medical diagnostics and analysis and in medical therapeutics, in many cases medical devices are used which, for example, have a diagnostic, analytical or therapeutic function and rely on one or more medical consumable items in order to carry out this function.

Examples of such medical systems are medical analysis devices which are used for the quantitative and/or qualitative detection of at least one analyte in a sample, for example for the detection of one or more metabolites in a body fluid. Glucose measuring devices shall be mentioned here as an application example, these devices being used to measure a glucose content for example in blood, interstitial fluid, saliva or urine.

Such analysis devices or others generally use one or more test elements by means of which the quantitative and/or qualitative detection of the analyte is effected. By way of example, said test elements can comprise one or more test fields which, upon contact with the analyte, carry out a specific chemically or physically detectable reaction or experience a specific, measurable change. Accordingly, the analysis devices can be designed to determine the analyte concentration optically, electrochemically or in some other way with the test elements. The test elements can be present, for example, as small test tubes, test strips, test tapes, test wheels having test fields arranged on a top side and/or a circumference, foldable test papers having a plurality of test fields, or in some other form. In this case, the test elements can be present individually or, for example, as a plurality in magazine form, where in the latter case a magazine with the test elements can also be regarded as a consumable item.

Another example of such medical systems with consumable items is lancet systems, in which, for example, a puncture aid functions as a medical device. Said puncture aid is generally designed to perforate part of a patient's skin by means of one or more consumable items in the form of lancets in order, for example, to generate a sample of blood or interstitial fluid.

Further examples of such medical systems are medication systems with metering devices. Such metering devices generally even operate with a plurality of types of medical consumable items. Thus, firstly, it is possible to use, for example, cartridges or other supply vessels of a medicament which is metered by means of the metering device. In this case, the medicament itself and/or the medicament with the corresponding vessel (for example the cartridge) can be regarded as a consumable item. One example of such metering devices is medication pumps, such as insulin pumps, for example. However, these metering devices generally furthermore require further types of medical consumable items, in particular catheters, for example.

Numerous further types of medical systems of this type, comprising a medical device and at least one consumable item, are known. One challenge for these medical systems, in practice, is that the medical device, in order to be able to interact with the consumable item correctly in order to carry out its medical function, requires information that can change. Thus, by way of example, test elements can differ from batch to batch, such that a batch-specific information component can be required for the correct evaluation of the quantitative and/or qualitative detection of the at least one analyte in the sample. This can be, for example, information about how the optical luminescence or absorption properties, i.e. e.g. the luminescence or color of a test field of a test element, changes with the analyte concentration. Electrochemical evaluation information components can also be encompassed. By way of example, current profiles and/or electrical potentials are measured in this case.

In the case of lancet systems, for example lancet systems with consumable items in the form of a lancet magazine having a plurality of lancets or in the form of an individual lancet, a puncture aid, for example, can require information about whether a correct type of consumable item has been inserted into the puncture aid, for example a lancet of a correct manufacturer or type. Generally, such information in the case of this type of consumable items or other types of consumable items can for example also be used for protection against counterfeiting in order to differentiate items of a correct or authorized manufacturer from "counterfeit" consumable items. This last, in addition to avoiding economic damage, can greatly reduce the risk of damage to health caused by counterfeit medical products.

In the case of medical systems comprising metering devices, for example insulin pumps, information about the type and/or the content of a cartridge of a medicament may be required, for example. If catheters or cannulas are used to meter the medicament, then a filling volume of the catheter may be required, for example, in order to ensure correct initial filling or flooding ("priming") of the catheter.

These are just a few examples of information components which can or have to be exchanged in the case of such medical systems. To solve this problem there are various possibilities in the prior art. Thus, in the case of commercially available glucose measuring devices, for example, an information carrier, for example a so-called ROM key, is enclosed with each batch of new test elements. The patient is required to enter said ROM key into the analysis device before using the new batch, such that correct information can be used for the evaluation of the measurement. However, this technique is associated with the risk, in principle, that, precisely in the case of older patients or children, the exchange of the ROM key fails to occur upon use of a new batch on the test strip. This can, since in this case possibly incorrect measurement results are output, have consequences with regard to an erroneous medication based on the erroneous measurement results.

The prior art therefore discloses various medical systems in which directly on the consumable material, that is to say not as a separate information carrier but rather fixedly connected to the consumable material, such an information carrier is provided. Since these information carriers, on account of a constantly increasing cost pressure in the medical sector, have to be completed in a cost-effective fashion and furthermore in a very small fashion, known electronic information carriers (such as radiofrequency labels for example) are ruled out in many cases.

Therefore, medical systems are known in which two- or three-dimensional optical codes are applied to medical consumable items, which can be read in by means of a corresponding optical code reader of the medical device. See, for example, U.S. Pat. No. 6,588,670 B2, the disclosure of which is hereby incorporated herein by reference in its entirety. Test strips equipped with corresponding barcodes as optical codes are also known. See, for example, U.S. Pat. No. 4,476,149 and U.S. Pat. No. 6,168,957, the disclosures of which are hereby incorporated herein by reference in their entireties. Reference may hereinafter be made to such optical codes by way of example.

One difficulty in the case of such optical codes have is that, in particular in medical handheld devices, the structural space available for the code reader is extremely limited. Moreover, the code readers have to be constructed in a very light fashion and have to be able to be manufactured cost-effectively in mass production. Numerous code readers for reading out optical codes are known from the prior art. See, for example, US 2006/0213994 A1 (code readers for DNA microarray scanners) and U.S. Pat. No. 7,175,091 B2 (code readers for check card readers), the disclosures of which are hereby incorporated herein by reference in their entireties.

Optically resolving proximity sensors, in particular in the form of so-called contact imaging sensors (CIS) are known from other fields of the art. For example, a thin image sensor is in the prior art in which an image of the object is generated on an image sensor by means of a microlens array. See, for example, US 2008/0088731 A1, the disclosure of which is hereby incorporated herein by reference in its entirety. Also, a fingerprint sensor is known in which a projection onto a CCD/CMOS structure is likewise effected by means of a microlens array. See, for example, US 2006/0202104 A1, the disclosure of which is hereby incorporated herein by reference in its entirety.

However, such code readers or image sensors have several disadvantages for use in medical systems of the type described above. This is because many of said sensors, in particular owing to the use of microlens arrays, necessitate a comparatively large structural space. Moreover, the production outlay for microlens systems is considerable, and the resolution of such microlens systems is generally inadequate for very small optical codes such as are required on test strips, for example.

In this case, one particular problem is posed in particular by the illumination required for many code readers. Illumination through a medical consumable item cannot be realized in numerous cases on account of the constitution of many consumable items, such as non-transparent test strips, for example. A reflective illumination of the optical codes is also ruled out for many medical systems since the available structural space in the case of the known systems and illumination techniques, does not allow the area of the optical code to be sufficiently illuminated.

Therefore, it is an object of the present invention to provide a medical system which at least substantially avoids the disadvantages of the medical systems described above. The medical system is intended to enable a reliable, structural-space-saving and cost-effective exchange of information between at least one medical consumable item and a medical device of the type described above.

SUMMARY

This object and others that will be appreciated by a person of ordinary skill in the art have been achieved according to the embodiments of the present invention disclosed and claimed herein. In one embodiment, the present invention comprises medical system comprising at least one medical device for carrying out at least one medical function. As set out above, the medical function can be any desired function usually required in the field of medicine or medical technology, in particular a diagnostic and/or analytical function and/or a therapeutic function. In this case, a diagnostic function can be understood to be a function which is aimed at determining at least one medical state of a patient. An analytical function can be understood to be virtually any desired measurement function which is aimed at measuring one or more parameters, for example of a sample. A qualitative and/or quantitative detection of at least one analyte in a liquid, solid or gaseous sample can be mentioned here as an example. A therapeutic function can be understood to be a function which is directed at influencing a body state of a patient in a targeted manner. This influencing will generally be aimed at improving the body state, that is to say healing, for example. Other types of influencing are also possible, however, for example influencing for cosmetic reasons. Medications can be mentioned as examples of therapeutic functions, for example administrations of medicaments by injection. However, other types of therapeutic functions are also possible, in principle, for example acupressures and/or acupunctures. For further examples of medical devices to which reference may also be made in the context of the present invention, reference may be made to the above description of the prior art. The medical device can also carry out a plurality of such medical functions, for example combinations of diagnostic and therapeutic functions. In order to carry out this at least one medical function, the medical device can be correspondingly configured by means of one or a plurality of mechanical devices and/or one or a plurality of electronic devices and/or one or a plurality of data processing devices, if appropriate designed in terms of program technology.

The medical device is designed to interact with at least one consumable item in order to carry out the at least one medical function. In this case, an interaction should be understood to mean a functional interaction, which does not necessarily require a physical connection between medical device and consumable item. However, such a physical connection can nevertheless be provided, for example in the form of a mechanical and/or electrical connection. Thus, by way of example, the medical device can comprise a holding device and/or a receptacle and/or a positioning device which receive and/or retain and/or position the at least one medical consumable item.

In this case, the medical consumable item is intended to be designed to enable or at least to support the medical function of the medical device. In other words, the consumable item can be designed to interact complementarily with the medical device in order, for example, to ensure the analytical and/or diagnostic and/or therapeutic function. In this case, the term "consumable item" should be understood to mean an item which can be produced on an industrial scale. Said consumable item is intended to be exchangeable as desired, whereas the medical device is generally suitable for multiple use. Thus, the consumable item can be provided, for example, for a single use or only for a limited number of uses.

The medical device furthermore comprises at least one code reader for reading out at least one information component of an optical code on the medical consumable item. In this case, an optical code should be understood to mean an information carrier which can be read out by means of light in the visible and/or infrared and/or ultraviolet spectral range of the electromagnetic spectrum, in particular a two- and/or three-dimensional barcode. Alternatively or additionally, numerous other types of optical codes can also be realized, for example barcodes, gray-scale codes or similar types of optical codes or combination of the abovementioned and/or other types of codes. The optical code can be applied, for example, on a surface of the medical consumable item, where a surface should analogously also be understood to mean that the optical code is covered by an at least partly optically transparent coating and can therefore still be wholly or partly optically read out. At all events, the optical code is intended to be able to be read out externally by means of electromagnetic radiation having a suitable wavelength.

The code reader of the medical device comprises at least one optical multi-channel evaluation unit, which is referred to hereinafter as image sensor for short. The image sensor comprises a plurality of sensors. These sensors, which can be arranged for example in a one- or two-dimensional fashion, for example in a one- or two-dimensional sensor array, are intended to be suitable for recording optical signals.

Alongside the image sensor, the code reader furthermore comprises at least one light-optical fiber plate. In this case, a light-optical fiber plate should be understood to mean an element which comprises a plurality of optical fibers, which may all be oriented parallel or substantially parallel. In this case, "substantially parallel" can, however, also be understood to include orientations that deviate from parallelism, for example by not more than 20°. In this case, in the context of the present invention, an optical fiber should be understood to mean an element which is transparent to light in the visible and/or infrared and/or ultraviolet spectral range and which acts as an optical waveguide in particular on account of total internal reflection. The light-optical fiber plate can comprise such optical fibers as a bundle, for example, wherein the optical fibers are fused, potted or adhesively bonded to one another, for example.

Preferably, said optical fibers are arranged in the light-optical fiber plate in such a way that they are arranged as densest packing at least in one dimension, such that the structural space is utilized to a highest possible degree by the light-optical fibers. Thus, by way of example, fibers having a round cross section can be arranged in a hexagonal arrangement. Other arrangements are also possible, however. The light-optical fiber plate can be configured as a planar plate, for example, that is to say as a disk-shaped element having a predefined thickness, which element has a lateral extent that is, in one embodiment, generally greater than the thickness of this fiber plate. By way of example, a plate having a polygonal, round or other cross section can be involved.

The special feature of such light-optical fiber plates is that they transport light from one side of the light-optical fiber plate, such as from a first plane of the light-optical fiber plate, to a second side of the light-optical fiber plate, such as to a second plane of the light-optical fiber plate, without appreciably changing the image in this case. Each end of a light-optical fiber acts at least approximately as a point light source which substantially reproduces the light conditions at its opposite end.

In this case, the code reader is constructed in such a way that the light-optical fiber plate is arranged in such a way that an image of the optical code is guided to the image sensor. The light-optical fiber plate is therefore arranged between the image sensor and the optical code, such that the optical code is transferred through the light-optical fiber plate as it were from that plane of the light-optical fiber plate which is adjacent to the optical code to the opposite plane of said light-optical fiber plate, in order to be recorded there by the image sensor.

In this case, the image sensor and the light-optical fiber plate can form one unit, which can also be configured in a very compact fashion. Thus, the image sensor and the light-optical fiber plate can be connected to one another to form the unit by means of a mechanical and/or positively locking and/or force-locking connection, for example. Image sensor and light-optical fiber plate, in particular the unit formed from these elements, can jointly have a thickness of less than 5 mm.

The sensors of the image sensor can form a linear arrangement, that is to say a one-dimensional arrangement, or else a two-dimensional arrangement, for example a matrix arrangement. In particular, the image sensor can comprise one or more of the following sensors: a CCD sensor, in particular a CCD array; a CMOS sensor, in particular a CMOS array, a photodiode sensor, in particular a photodiode array; an organic photodetector, in particular an organic photodiode, in particular an array of such organic photodetectors. In principle, however, it is also possible to use other types of imaging sensors which are based on other physical principles, or combinations of the abovementioned and/or further imaging sensors.

In one embodiment, the light-optical fiber plate is applied directly to the image sensor. In one refinement, the distance between the image sensor and the light-optical fiber plate is less than a distance between adjacent sensors of the image sensor. Since the light-optical fiber plate, on its side facing the image sensor, substantially identically reproduces the light conditions on its side remote from the image sensor, this arrangement is tantamount to an arrangement in which the image sensor bears substantially directly on the code. In contrast to the latter arrangement, however, the light-optical fiber plate, as will be explained in greater detail below, affords the possibility of bringing about coupling-in of light through the light-optical fiber plate, such that the code can be efficiently illuminated.

In principle, the light-optical fiber plate can be produced from any desired transparent material. In particular, plastics materials and/or glasses can be used. These can also be configured in a core-cladding structure, wherein, by way of example, the claddings of the individual optical fibers are fused or adhesively bonded to one another and form a common matrix of the light-optical fiber plate into which the actual fiber cores are embedded. In one embodiment, the optical fibers and/or the cores thereof which are embedded in the optical fiber plate have a diameter of less than about 100 µm, and in other embodiments the diameter is about 80 µm or less.

The code reader can furthermore have at least one illumination device, that is to say a device which is configured for illuminating the optical code of the consumable item. Preferably, this illumination is effected on one side, from the same side on which the image sensor is also provided. In this case, in contrast to transillumination devices, the entire code reader can be configured in a very compact fashion, wherein the medical consumable item has to be led to the code reader only on one side. This illumination from the detector side, that is to say from the side of the image sensor, thus affords advantages with regard to the structural space. These advantages, as described above, are supported by the use of the light-optical fiber plate since an illumination through the light-optical fiber plate can be effected without adversely affecting the quality of the image recording of the code or the structural space requirement. Alternatively or additionally, other types of illumination are also possible, however.

The illumination device can correspondingly comprise at least one light source, which can be arranged in various ways. A plurality of light sources having different arrangements and/or different spectral properties can also be provided. Thus, firstly, the light source, as known from the prior art, can be used as a transmitted-light light source and can be designed to transilluminate the medical consumable item in the region of the optical code. In this case, the consumable item, in this region, should be at least partly transparent to the wavelength used or be able to transport at least the light of the light source at least partly to the optical code. Various exemplary embodiments of such medical consumable items or of carrier materials which satisfy these requirements will be described below. Alternatively or additionally, however, as will be explained in greater detail below, a light source for illumination on one side is also possible.

As set out above, light having a wavelength in the visible and/or infrared and/or ultraviolet spectral range can be used for the illumination. The spectral range in the range of between 300 nm and 3000 nm is appropriate, in particular. Suitable light sources can be used for this purpose, in particular one or a plurality of light-emitting diodes on an inorganic and/or organic semiconductor basis, in particular also as light-emitting diode arrays. Other types of light sources can also be used, for example lasers, in particular semiconductor lasers.

The illumination device can be configured as a monochromatic illumination device, but can also be designed to illuminate the medical consumable item with light having different wavelengths. In this case, "different wavelengths" should be understood to mean spectral properties in the case of which the spectral profile of the light at least does not completely correspond, for example by virtue of the peak wavelengths differing from one another. In particular, the illumination device can be designed to illuminate the medical consumable item, in particular the optical code there, simultaneously or else sequentially, i.e. at different points in time, with light having different wavelengths. However, simultaneous illumination with light having different wavelengths is also possible, in principle, for example in association with a corresponding spectral separation by the image sensor and/or some other wavelength-selective element, for example one or more filters and/or one or more dichromic mirrors. Various configurations are possible.

Furthermore, alternatively or additionally, the code reader can also be designed to carry out a challenge-response scheme. Thus, the code reader can be designed, for example, to record the image of the optical code in a time-delayed manner with respect to an illumination by the illumination device. Thus, by way of example, a circuit can be provided in which a signal recording by the image sensor only begins if the illumination by the light source is switched off. By way of example, a pulsed scheme can be used, with an excitation pulse of, for example, less than 100 μsec. A measurement can then be begun in a manner offset by a temporal offset, for example of 200 μsec, after the end of the excitation pulse. Such a challenge-response pulsed scheme can be used, in particular, in the case of luminescent codes, for example in the case of codes which comprise one or a plurality of modules having fluorescent and/or phosphorescent media, e.g. from the group of the complexes of rare earths such as europium, for example.

As explained above, the illumination by the illumination device can be effected on one side, in particular, that is to say that the illumination is effected from the same side of the medical consumable item as the observation by means of the light-optical fiber plate and the image sensor. This can be realized in various ways. In particular, the illumination can be effected through the light-optical fiber plate. By way of example, this can be realized by the light-optical fiber plate being illuminated by at least one light source of the illumination device from the side, that is to say for example at about 90° with respect to the orientation of the optical fibers in the light-optical fiber plate or at an angle which deviates from a right angle by not more than about 20-30°.

Alternatively or additionally, however, the illumination can also be effected substantially parallel to the optical fibers of the light-optical fiber plate. This can be done, for example, by illumination being effected laterally past the image sensor through the light-optical fiber plate. Alternatively or additionally, however, illumination can also be effected through the image sensor, such that the excitation light penetrates through the image sensor first of all and then the light-optical fiber plate. This can be done, for example, when the image sensor is at least partly transparent to the employed excitation light of the light source of the illumination device. For this purpose, by way of example, corresponding openings can be provided in the image sensor, through which openings the excitation light can pass in order then to reach the medical consumable item and the code through the light-optical fiber plate. Alternatively or additionally, however, the material of the image sensor itself can also be at least partly transparent to the excitation light. By way of example, the image sensor can have a semiconductor material (e.g. silicon) having a band gap, wherein the light source is designed to emit light having a lower energy than the band gap. In other words, the image sensor is designed in such a way that it substantially does not absorb the excitation light of the light source or absorbs it only to an insignificant extent, for example to an extent of not more than 20%. In the case of silicon, this can be done, for example, by using light having a wavelength of more than 1000 nm. If the energy of this excitation light does not suffice for reading out or adequately illuminating the optical code, then the optical code can comprise corresponding light converters which, by way of example, generate shorter-wave photons from the longer-wave photons of the excitation light of the light source, for example in the context of multiphoton processes.

As an alternative or in addition to an illumination through the light-optical fiber plate, however, the illumination device can also be designed to illuminate the optical code from the side, that is to say substantially perpendicularly to a viewing direction of the light-optical fiber plate. This can be effected, for example, through a carrier material of the medical consumable item in the region of the optical code, for example once again through a carrier material that conducts the excitation light of the light source of the illumination device or is transparent to said excitation light.

Alternatively or additionally, there is furthermore, as explained above, of course also the possibility of illuminating the medical consumable item at least in the region of the optical code from the rear side, that is to say from the side remote from the light-optical fiber plate and the image sensor. In this case, an at least partly transparent or light-conducting carrier material may be employed in this region of the medical consumable item. This type of illumination, which can be used as an alternative or in addition to the other types of illumination, can predominantly be utilized for an absorptive detection of the optical code, but also for a luminescence detection, for example.

The image sensor can furthermore have at least two regions having a differing spectral sensitivity. By way of example, the image sensor can comprise different sensors having a differing spectral sensitivity. In this way, by way of example, a plurality of light wavelengths which are reflected or emitted or emerge in some other way from the optical code can be utilized for detection. By way of example, these different sensitivities can be achieved by means of intrinsically different sensitivities of the sensors, or it is possible to use one or more filters for producing these different spectral sensitivities. Generally, the code reader can have at least one optical filter, in particular a cut-off filter and/or an interference filter.

The optical code of the medical consumable item can be composed, in particular, of a plurality of optically readable modules as smallest information unit. This smallest information unit can correspond to a "bit" for example. As described above, the code can be constructed in a one- or two-dimensional fashion, for example, such that a module in one or two dimensions constitutes the smallest unit to be resolved by the code reader.

In one embodiment, at least three optical fibers are provided per module in each dimension which is utilized for representing information components. Thus, for example in the case of a two-dimensional code, at least nine fibers can be provided per module. The modules can have, in the case of a one-dimensional code, for example, a line form, wherein the minimum line width of the lines used corresponds to the width of a module. In the case of a two-dimensional code, the modules can be configured for example as round or rectangular, in particular square, wherein the smallest edge length of a square corresponds to the dimension of a module. By way of example, modules having a width of 300 µm can be used.

In this case, the light-optical fiber plate may be configured and positioned relative to the optical code in such a way that said light-optical fiber plate provides a sufficient resolution for reading out the optical code. This can be ensured, in particular, by the medical device and/or the code reader and the medical consumable item being positioned with respect to one another in such a way that a distance between the light-optical fiber plate and the optical code is less than a distance between the midpoints of adjacent modules of the code. In other words, the average free path length which has to be covered by photons from the modules of the code to the light-optical fiber plate is intended to be less than the distance between the midpoints of adjacent modules, that is to say the dimensions of the optical code which are to be resolved.

Generally, the medical system can comprise a positioning device. Said positioning device can be designed to position the consumable item and the medical device relative to one another, for example to enable optimum reading of the optical code. By way of example, the positioning device can be designed to position the medical device and the consumable item relative to one another in such a way that, in a read position, the above-described condition with regard to the distance between the light-optical fiber plate and the optical code and the distance between the midpoints of adjacent modules of the code is met. Alternatively or additionally, the positioning device can also be designed, for example, always to ensure a constant distance between the consumable item and the light-optical fiber plate, including an optional tolerance range for incorrect positioning, for example.

By way of example, the positioning device can be designed always to ensure a certain minimum distance between the light-optical fiber plate and the consumable item. This can be advantageous in particular in the case of test elements, such as test strips, for example, which can be inserted in particular into the medical device. If insertion takes place with an excessively small distance between the test element and the light-optical fiber plate, then this can lead for example to damage (for example wear and/or scratching) of the light-optical fiber plate and/or to contamination thereof, for example by blood clinging to the test element. This can be prevented by means of a suitable configuration of the positioning device.

Thus, the positioning device can comprise, for example, at least one spacer which always ensures a minimum distance between the medical consumable item, for example the test element, and the code reader, for example the light-optical fiber plate of the code reader. Said spacer can comprise, for example, at least one rail (in particular a spacer rail), at least one attachment, at least one guide, at least one spacer lamina and/or at least one spacer ring or else combinations of the abovementioned elements and/or further elements.

In order, on the other hand, to ensure that the distance between the medical consumable item and the code reader, in particular the light-optical fiber plate, does not exceed a maximum distance, oppositely acting elements can be provided in the positioning device. Thus, the positioning device can comprise, for example, at least one press-on element which applies to the medical consumable item a force acting in the direction of the code reader. By way of example, the press-on element can be configured for pressing the consumable item against the spacer described above. Alternatively or additionally, an opposite application of force is also possible, that is to say an application of force wherein the press-on element has the effect that the code reader is pressed wholly or partly against the medical consumable item. Thus, by way of example, the light-optical fiber plate and/or a unit comprising the light-optical fiber plate and the image sensor can be pressed against the consumable item by the press-on element. Generally, the press-on element can comprise, for example, one or more spring elements, one or more elements of elastic materials or similar elements which are usually used for an application of force.

The positioning device can be, for example, a constituent part of the medical device. The positioning device can be adapted to the type of medical device and/or the type of medical consumable item and comprise different types of mechanical devices. By way of example, the positioning device can comprise holding devices in order to retain the medical consumable item on and/or in the medical device in such a way that the medical consumable item is positioned in the read position, whilst complying with the condition described above. By way of example, the positioning device can correspondingly comprise at least one rail for introducing the medical consumable item, for example a test element. The positioning can also be a lateral positioning, that is to say for example a positioning in a plane perpendicular to the connection between image sensor and consumable item. Alternatively or additionally, the positioning device can also comprise a bearing area on which or at which the medical consumable item can be placed or laid such that the consumable item is positioned in the read position.

The code reader can be designed in such a way that the optical code is completely imaged in an active sensor surface of the image sensor. This can be effected, in particular if the light-optical fiber plate does not have a magnifying or demagnifying effect, for example by the active sensor surface of the image sensor being at least exactly the same size as the area of the optical code. Alternatively or additionally, however, the light-optical fiber plate can also have a magnifying or demagnifying effect, such that the image of the optical code which is generated by the optical fiber plate on the side facing the image sensor is larger or smaller than the actual optical code.

Alternatively, it is also possible for only a part of the image of the optical code to be imaged on the image sensor. By way of example, once again in this case the image sensor with its active area can be smaller than the optical code, or it is possible to implement a magnifying or demagnifying effect by the light-optical fiber plate which brings this about. In this case, the image sensor records only a partial region of the optical code. The optical code can comprise repeating, at least partly redundant information components. By way of example, the optical code can comprise repeating bit patterns or patterns of modules, wherein these repeating bit patterns or patterns of modules can be designed in such a way that at least one of said bit patterns or module patterns is completely imaged onto the active sensor surface of the image sensor.

Further developments of the invention concern the configuration of the medical consumable item, at least in the region of the code. Thus, the code and/or the optically readable modules of the code can be applied to the medical consumable item in particular by means of one or more of the following methods: a printing method onto a surface of the medical consumable item; a laser-induced dye conversion method; a mechanical deformation of a surface of the medical consumable item or of the medical consumable item itself. However, other methods can also be used, in principle, such as, for example, mechanical ablation methods, ablation also by laser processing, implantation methods, photolithography or similar methods.

The medical consumable item can comprise, in the region of the optical code, a carrier material having transparent and/or light-scattering properties. This means that the carrier material should be at least partly transparent and/or light-scattering in particular for light of at least one light source of the illumination device.

The optical code itself, for example the modules of the optical code, can also be wholly or partly designed to interact differently with light having different wavelengths. In particular, it is correspondingly possible to use materials for the optical code or the modules which have, for example, different excitation wavelengths, different absorption properties, different scattering properties or optical properties that are different in some other way for excitation light of the illumination device.

The optical code can interact with light in various ways. Thus, the optical code can have, for example, at least partly luminescent properties, that is to say for example phosphorescent and fluorescent properties. For this purpose, the optical code, in particular the modules of the optical code, can have corresponding dyes, pigments, phosphors or the like. Alternatively or additionally, the optical code, in particular the modules of the optical code, can comprise at least one light converter which is designed to convert an excitation light, for example an excitation light of the illumination device, and/or ambient light, into a light having a different wavelength than the excitation light. In other words, the light converter can comprise, for example, an up-converter or a down-converter, that is to say a converter which can convert light into higher-energy light or lower-energy light. Said light converter can, for example, in turn be present in the form of a dye, a pigment, a phosphor or in a similar form. In this way, by way of example, an excitation of the light converter can be effected by means of a corresponding excitation light, and this excitation can be detected by the code reader and/or the image sensor in order to read out the information of the code.

Further developments concern the surroundings of the code, that is to say the region of the medical consumable item in which the optical code is applied. Thus, the medical consumable item can comprise in this region, for example, a carrier material having diffusely light-conducting and/or transparent properties, in particular for excitation light, for example excitation light of the illumination device. In particular, the carrier material can comprise a polyester, for example Melinex. The carrier material, in particular the polyester, can furthermore also be doped, for example with titanium dioxide ($TiO_2$). As a result, by way of example, a substantially white overall impression of the carrier material can arise, wherein the carrier material nevertheless has diffusely light-scattering properties. By way of example, a uniform illumination of the code can be ensured in this way.

Similarly to the possible configuration of the code and/or the modules of the code, the medical consumable item can also comprise, in the region of the optical code, a carrier having a carrier material, wherein the carrier can furthermore comprise at least one light converter in this region. Said light converter, which can in turn be an up-converter and/or a down-converter in accordance with the above description, can be designed, in particular, to convert excitation light into a light having a different wavelength. The light converter can be distributed uniformly in the carrier material, for example, such that light having the different wavelength than the excitation light illuminates the optical code substantially uniformly. In this case, "substantially uniformly" can be understood to mean an isotropic illumination in which the illumination of the code deviates from a uniform illumination by less than 20%.

Further configurations of the invention concern the configuration of the medical device and/or of the medical consumable item. For this purpose, in particular the medical systems mentioned in the description of the prior art are appropriate in many embodiments. Thus, the medical device can comprise, for example, an analysis device for detecting at least one analyte in a sample, for example a liquid sample, in particular a body fluid. In particular metabolites in the body fluid, for example glucose, cholesterol and/or similar metabolites, are appropriate as analyte. A detection of coagulation is also possible, by way of example. The analysis device can then be designed to interact with a medical consumable item in the form of at least one test element, in particular a test strip and/or a test tape. In this case, an individual test strip can be understood as a medical consumable item, or else, as explained above, a plurality of test strips and/or test tapes which, for example, can be accommodated in a corresponding magazine or a housing. In the latter case, the magazine and/or the housing can also correspondingly be provided with the optical code.

Alternatively or additionally, the medical system can also comprise a metering device for metering at least one medicament, in particular a medication pump, for example an insulin pump. In this case, the consumable item can comprise, for example, a catheter and/or a cannula (both terms are used synonymously in the following description) with which the metering device interacts. The medical system can correspondingly be configured, for example, as a so-called "infusion set". Since catheters are usually supplied in a manner filled with air, it is necessary, before application on and/or in the body, to carry out flushing with a medical liquid, such as an insulin infusion, for example, in order at least substantially to displace the air from the catheter. The filling volume specific to the respective catheter can be entered manually into the metering device, for example the metering pump, such that a corresponding metering for flushing through the catheter is effected. This flushing process is referred to as "priming". However, as explained above, the manual entry of the priming parameters is fraught with risk since this manual entry can, for example, take place erroneously or not at all. Therefore, automatic priming ("auto-priming"), as disclosed in WO 2007/128144, for example, is useful in many embodiments. According to the invention, therefore, the code reader can be designed and utilized for reading out at least one information component concerning a filling volume of the catheter from the optical code, which can be applied, for example, on the catheter or a packaging of the catheter. The auto-priming can be considerably simplified in this way.

Generally and independently of the remaining configuration of the medical system, the information read out from the optical code by the code reader can comprise a multiplicity of possible information components. By way of example, but not exhaustively, the information can comprise a batch-specific information component concerning the medical consumable item. In this case, a batch-specific information component should be understood to mean an information component which can generally change from medical consumable item to medical consumable item. By way of example, this information component can comprise an information component concerning a batch, an information component concerning batch-specific special features of the medical consumable item, an information component concerning a manufacturer, a number (for example a serial number), a production parameter, an information component concerning the manner in which the functionality of the medical device is to be adapted to the specific batch of the medical consumable item, or the like. Alternatively or additionally, a batch number of the medical consumable item can be encompassed. Furthermore, likewise alternatively or additionally, at least one mathematical parameter and/or parameter set can be encompassed which is required by the medical device for a correct interaction between the medical device and the medical consumable item. Furthermore, likewise alternatively or additionally, a date and/or an expiration date can be encompassed. Moreover, likewise alternatively or additionally, an instruction to a user of the medical system can be encompassed, for example an information component concerning what type of medical consumable items is actually used and/or how this medical consumable item is to be handled. This instruction can also be issued to the user for example by means of an indicator device of the medical device, for example a visual and/or acoustic indicator device. Furthermore, likewise alternatively or additionally, a manufacturer information component can be encompassed, such that, by way of example, protection against counterfeiting can also be implemented by means of the medical system. In this way it is possible, by way of example, to prevent the use of counterfeit medical consumable items, that is to say medical consumable items originating from non-authorized manufacturers, which can result in fatal consequences. In this case, the medical system can, for example, in turn be designed to inform a user of the medical system about the manufacturer and/or about the fact that a counterfeit is present, and/or to implement other suitable measures, for example a disabling of one or more functionalities and/or a documentation of the use of the counterfeit consumable item. Furthermore, the information, likewise alternatively or additionally, can also comprise a calibration information component, wherein a calibration information component should generally be understood to mean information components concerning how, for example, measurement results obtained by the medical device by means of the medical consumable item (for example a test element) are to be evaluated. In this case, too, batch-specific differences can again be taken into account.

The medical device can be configured, in particular, as a handheld device, that is to say as an device which a user can hold by hand without the aid of transport devices. In this case, the low weight and the compactness of the code reader user become apparent in a particularly advantageous manner. The handheld device can also comprise at least one electrical energy store, in particular a battery and/or a rechargeable battery.

In accordance with the type of medical system, the medical consumable item can be configured in many different ways. It is also possible for a plurality of different types of medical consumable items to interact with the medical system, wherein different code readers can be used for the optical codes of the different consumable items, or wherein one and the same code reader can also be used for the different types of medical consumable items.

Thus, the medical system can comprise at least one medical consumable item having at least one optical code which can be read out by the code reader, wherein the medical consumable item can comprise, for example, one or more of the following consumable items: a test element for detecting at least one analyte in a sample, in particular a test strip or a test tape; a magazine for receiving at least one test element for detecting at least one analyte in a sample, in particular a test strip or a test tape; a lancet for producing an opening in a surface of a patient's skin; a magazine for receiving at least one lancet for producing an opening in a surface of a patient's skin; a medicament packaging, in particular an insulin cartridge; a catheter and/or a cannula.

Thus, the medical consumable item can comprise, for example, a test element, in particular a test strip and/or a test tape and/or a test wheel and/or a foldable test element, for detecting at least one analyte in a sample. Reference may be made to the above description of the prior art by way of example. As set out above, the test element can conduct a quantitative and/or qualitative detection of the analyte for example by means of an optical test and/or an electrochemical test. As an alternative or in addition to individual test elements, magazines for receiving at least one test element of this type can also be provided, wherein the magazines can also be coded as consumable items.

As an alternative or in addition to test elements, the medical consumable item can, for example, also comprise a lancet for producing an opening in a surface of a patient's skin or a magazine for receiving at least one lancet of this type. Furthermore, the medical consumable item can comprise a medicament packaging, in particular a packaging for liquid medicaments. By way of example, said medicament packaging can comprise an insulin cartridge. Furthermore, as set out above, the medical consumable item can comprise a catheter, for example.

The medical system in accordance with one or more of the advantageous embodiments described above has a multiplicity of advantages over known medical systems of this type. Mention has already been made of, in particular, the compactness and the configuration of the system with a low weight, which becomes apparent in an advantageous manner in particular in the case of handheld devices. Thus, for the code reader, for example, it is possible to achieve a structural size of 1 cubic centimeter or less.

Furthermore, the solution according to the invention is also suitable for a large information depth. The suitability is optimal, for example, for information components of 20 to 100 bits. By way of example, it is possible to use information components of 40 bits of useful information and 40 bits of check and redundancy information, that is to say a total of 80 bits. In this case, the area of the optical code can be 10 to 100 $mm^2$, for example. As a result, it is firstly possible, as mentioned above, to realize or use code readers of small design. Furthermore, the requirements made of the technology with which the optical code is applied, for example the printing technology and/or the other application methods mentioned above, are thereby reduced, which, for example, also enables more cost-effective production.

The illumination of the optical code can be effected by a very short route and nevertheless ensure a sufficient homogeneity of the illumination. In this way, a reliable read-out of the code can be ensured, which contributes overall to the operational and handling reliability of the medical system. The medical device can comprise one or more controllers, for example one or more data processing devices, which effect conversion of an image of the complete or partial optical code recorded by the image sensor into the corresponding information component, such that this information component of the optical code can be read out. The controller can be integrated in the code reader, or can also be combined wholly or partly with other controllers of the medical device, for example with a central controller present anyway in many medical devices, such as glucose measuring devices, for example. In particular, illumination and evaluation functions can also be integrated into a single module, for example a single module of the code reader. This single module can then be brought very close to the medical consumable item, in particular the optical code thereof, such that not only the code reader itself but also the code reader including the optical code, on the medical consumable item, occupies a comparatively small structural space, for example a structural space of approximately 1 cubic centimeter.

The code reader in certain embodiments manages completely without imaging systems, that is to say without lens systems, in particular microlens systems, or without curved mirrors, or the like. Such imaging systems can be completely dispensed with by virtue of the use of the light-optical fiber plate, since, by means of the light-optical fiber plate, the image sensor can be placed directly virtually onto the optical code. This, too, contributes considerably to reducing the structural space.

The possibility of the above-described temporally resolved measurement, for example by means of a challenge-response pulsed scheme, enables a measurement even in the case of unfavorable light conditions. Thus, by way of example, by means of said pulsed scheme, using a pulse and the measurement of the persistent light, it is possible to improve the ratio of useful signal and noise signal since, by way of example, the problem of a stray light background is reduced. The signal quality and the reliability of the information read out are thereby improved.

Furthermore, the medical system is substantially indifferent to the type of coded information. As explained above, this information can comprise a batch-specific information component, for example. The coded information can be, for example, binary-coded, in particular two-dimensionally. The high spatial resolution makes it possible to ensure a high storage density of the information in the optical code.

As explained above, the evaluation of the optical code by means of the code reader can also have recourse to complex measurement schemes. Thus, as set out, it is possible to use temporally resolved measurement schemes, for example. Alternatively or additionally, it is possible to use wavelength-selective measurement schemes, for example using a plurality of excitation wavelengths, using a plurality of excitation wavelengths, using a plurality of response wavelengths coming from the optical code or the modules, or by means of combinations of these methods. Alternatively or additionally, the code can also be obtained by means of a mechanical configuration, for example by means of a flat, deformed, hollow or similar mechanical configuration of a surface of the medical consumable item in the region of the optical code.

Furthermore, the medical system, in particular the code reader of this medical system, has a high flexibility with regard to the illumination of the optical code. As explained above, by way of example, an illumination device can be used for this illumination. Alternatively or additionally, light sources present in a different way can also be utilized, for example ambient light. By way of example, the illumination can be effected wholly or partly through the medical consumable item, diffusely within the consumable item, diffusely through the light-optical fiber plate, from the side of the light-optical fiber plate, through the light-optical fiber plate, through the image sensor or by means of a combination of the abovementioned types of illumination or other types of illumination.

It has been described above, in one embodiment of the medical system, that an illumination can also be effected through the image sensor. As is immediately clear to the person skilled in the art, this configuration of an illumination through the image sensor can also be applied to other medical systems or other medical devices in which a combination of an image sensor with an illumination device is provided. In this case, these medical systems or medical devices need no necessarily comprise a code reader or a light-optical fiber plate.

Alongside medical systems and medical devices comprising code readers, medical devices in which a test element, for example, is evaluated by means of the image sensor can be mentioned by way of example here. For example, said test element can comprise at least one test field, with at least one test chemical which is suitable for a qualitative and/or quantitative detection of at least one analyte in a sample, for example a body fluid. Such test elements are sufficiently known as test strips, for example, from the prior art. These can also be evaluated by means of one or a plurality of image sensors. By way of example, the at least one test field can change a color or some other optical detectable property when the at least one analyte is present. Additionally in this case or in other cases, an illumination of the article viewed by the image sensor, whether it be a barcode, a test field or some other type of article, is therefore generally necessary here. Without restricting further possible types of the interaction of the light with the article, which interaction can be of reflective type, transmissive type or exciting type, for example, the light applied to the article is referred to hereinafter as excitation light.

Therefore, a medical device for carrying out at least one medical function is proposed in a further aspect of the present invention. For the possible configuration of this medical function or the configuration of the medical device, reference may be made to the above description by way of example. In particular, the medical device can be used in a medical system in accordance with one or more of the configurations described above. However, other fields of use are also possible, in principle.

The medical device comprises at least one image sensor having a plurality of sensors. Furthermore, the medical device comprises at least one illumination device, which, for its part, has at least one light source. The light source is designed to illuminate at least one article, in particular a medical consumable item, through the image sensor.

As explained above, the at least one article can be configured in various ways. By way of example, it can be a medical consumable item, in particular a medical consumable item having at least one barcode. Alternatively or additionally, however, the article can also be at least one test element with at least one test field which is designed for detecting at least one analyte in a sample, in particular for detecting at least one analyte in a body fluid. Various configurations are possible.

The illumination of the article through the image sensor can be realized in various ways, wherein reference may once again be made by way of example to the above description of the medical system and there in particular to the description of the image sensor and/or of the illumination device. However, other configurations are also possible. Thus, by way of example, the image sensor itself can be at least partly transparent to an excitation light of the light source. The image sensor can have a plurality of openings through which excitation light of the light source can pass. Alternatively or additionally, the image sensor can have a material which is at least partly transparent to excitation light of the light source. The image sensor can have, in particular, a semiconductor material having a band gap, wherein the light source is designed to emit light having a lower energy than the band gap.

Independently of the use of the light-optical fiber plate, therefore, the illumination of the article through the image sensor affords the possibility of achieving firstly a sufficient and as homogeneous as possible an illumination of the article or at least of a relevant region of the article, for example of a test field.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
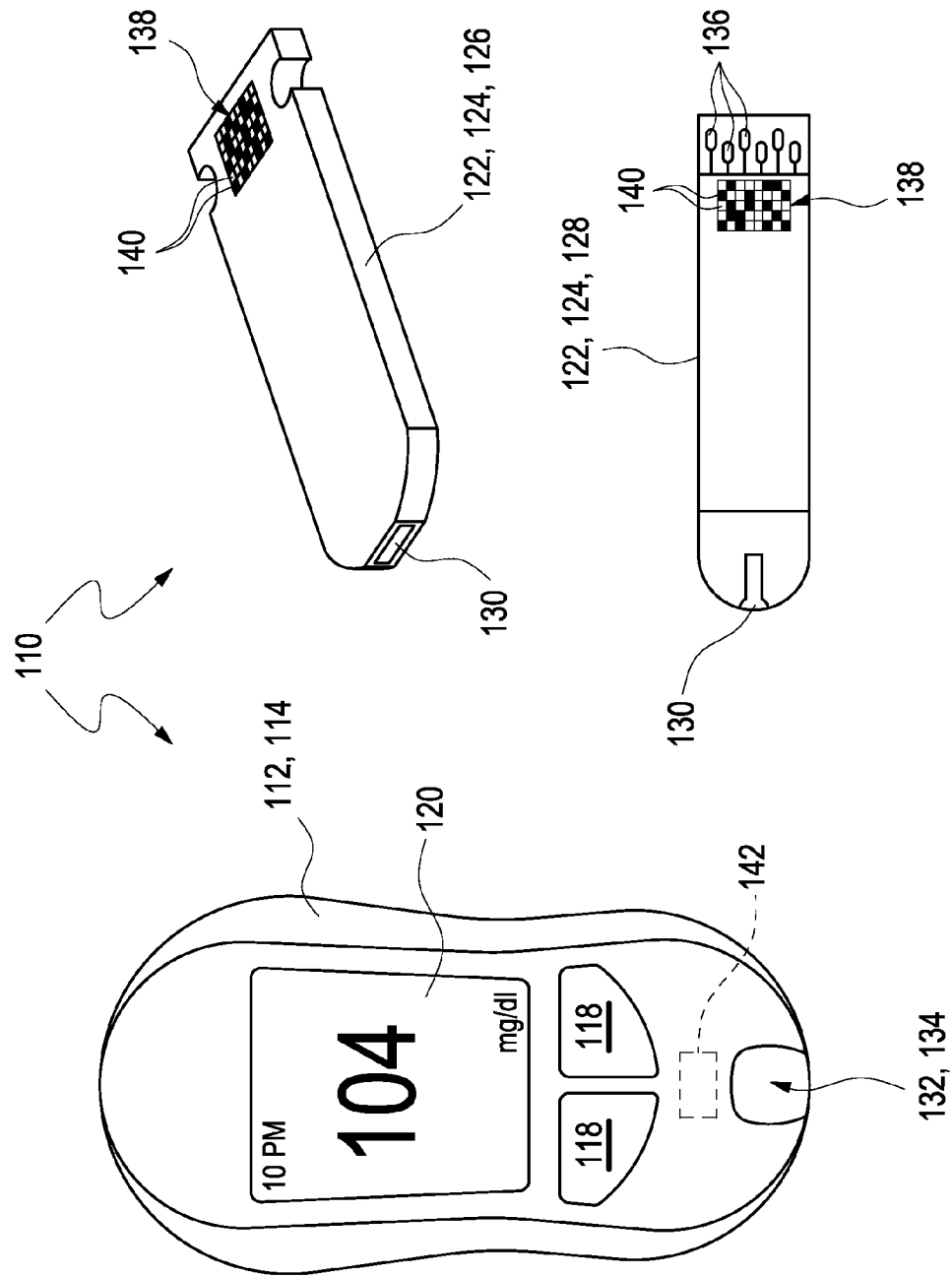
FIG. 1 shows a first exemplary embodiment of a medical system according to the invention with a blood glucose measuring device.
Figure 2:
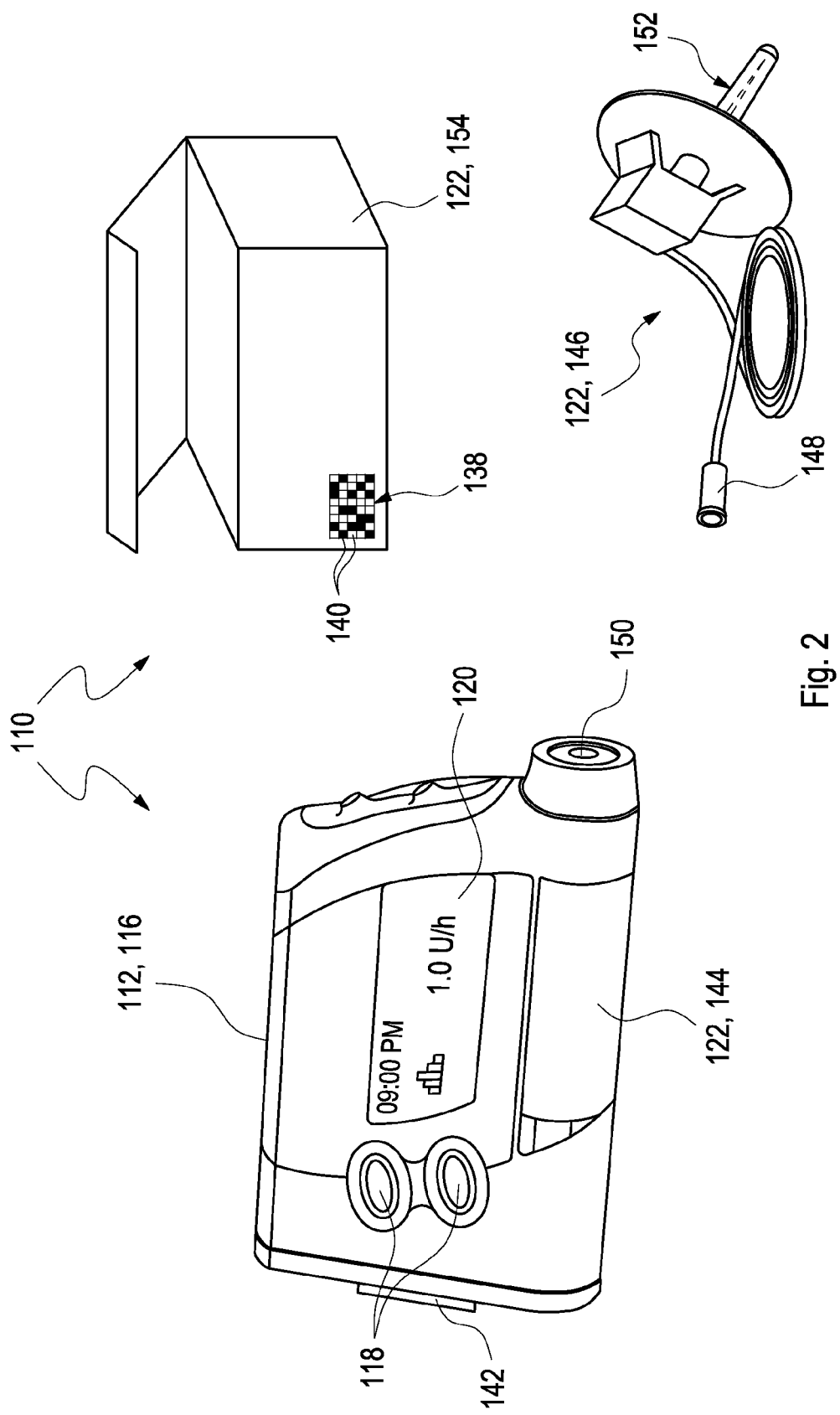
FIG. 2 shows a second exemplary embodiment of a medical system with an insulin pump and an infusion set.

FIGS. 1 and 2 illustrate by way of example two different embodiments of medical systems 110 according to the present invention. These medical systems 110 each comprise a medical device 112, which is the actual function carrier of a main function of the medical system 110. In this case, by way of example, in the exemplary embodiment in FIG. 1, the medical device 112 is configured as a blood sugar measuring device 114, whereas the medical device 112 in the exemplary embodiment in accordance with FIG. 2 is configured as an insulin pump 116. The medical device 112 can be configured, in particular, for enabling an interaction with a user. By way of example, the possibility of operating mechanical and/or electrical functions of the medical device 112 can be made possible for a user by input means 118. Furthermore, output means 120 can be provided, for example one or more displays, which enable, for example, measurement values, set parameters or other information to a user. The medical device 112 can therefore constitute the actual "interface" of the medical system 110 in relation to the user.

In addition, the medical system 110 comprises one or more medical consumable items 122. In the case of the medical system illustrated in FIG. 1, the blood sugar measuring device 114 interacts for example with test elements 124, which are shown by way of example in two embodiments in FIG. 1. While the upper embodiment, designated by the reference numeral 126, shows a stiff test element having a flat, elongate shape, the lower embodiment in FIG. 1 shows a test strip 128. The blood sugar measuring device 114 illustrated in FIG. 1 is generally designed for the use of test strips 128, but other types of test elements, for example the test element 126, can also be used.

Both test elements 124 have an application location 130, at which a sample of a body fluid can be applied to the test element 124. This can be effected when the test element 124 has been introduced into the blood sugar measuring device 114, or else, in different systems, outside the blood sugar measuring device. The blood sugar measuring device 114 has an introduction opening 132, which simultaneously serves as a positioning device 134, in order, in the case where the test element 124 has been correctly inserted into the introduction opening 132, to enable an interaction of the blood sugar measuring device 114 with the test element 124.

The evaluation of the sample applied to the application location 130 can be effected optically or electrochemically, for example. In the case of the test strip 128, electrode contacts 136, for example, are provided for this purpose, contact being made with said electrode contacts by the blood sugar measuring device 114 when the test strip 128 has been inserted into the blood sugar measuring device 114.

Since the test elements 124 can change from batch to batch, it is proposed to apply an optical code 138 on the test elements 124. In the exemplary embodiments illustrated, said optical code 138 is merely indicated symbolically and can be configured as a two-dimensional barcode, for example. The code can be a 35-bit code composed of 5☐7 smallest units, for example. Said smallest units are also referred to as modules 140. These smallest units, which can be "white" or "black", for example, in the embodiment illustrated, contain the actual information in binary form, for example. Alternative configurations are also possible, for example by using intermediate levels between black and white, that is to say gray-level or corresponding color gradations. The terms black, white, gray and color are correspondingly analogously applicable in the entire wavelength range of 300-3000 nm.

As a counterpart to the optical code 138, the medical device 112 in the form of the blood sugar measuring device 114 comprises a code reader 142, which is merely indicated in FIG. 1. Said code reader 142 can be arranged, for example, in the vicinity of the introduction opening 132 within a housing of the blood sugar measuring device 114, such that in a fixed position when the test element 124 has been inserted into the positioning device 134 (static measurement) or during the insertion of the test element (dynamically), the optical code 138 can be read out by the code reader 142. By way of example, said code reader 142 can be a code reader for 5☐7 pixels. Exemplary embodiments of the code reader will be described in greater detail below:

In the case of the exemplary embodiment in accordance with FIG. 1, the test element 124 should be regarded directly as a medical consumable item 122, on which the optical code 138 is applied. Alternatively or additionally, however, the optical code 138 can also be arranged, for example, on a medical consumable item 122 in the form of a packaging of the test elements 124. In this case, the code reader 142 can be configured, for example, wholly or partly as a code reader which is fitted on an outer side of a housing of the blood sugar measuring device 114 and which is designed, for example, to read out the optical code 138 on said packaging.

Three different embodiments of medical consumable items 122 are illustrated by way of example in the case of the medical system shown in FIG. 2. Thus, there is firstly the possibility of configuring an insulin cartridge 144 as a medical consumable item 122. In this case, too, an optical code 138 (not illustrated in FIG. 2) can be applied on said insulin cartridge 144. Alternatively or additionally, however, it is also possible to use a primary cartridge for an insulin supply, wherein insulin is transferred from said primary cartridge into the insulin cartridge 144. In this case, by way of example, the primary cartridge from which insulin is transferred into the insulin cartridge 144 itself or a packaging thereof can be coded with an optical code 138 and thus act as a medical consumable item 122.

In addition, FIG. 2 illustrates a medical consumable item 122 in the form of an infusion set 146. This infusion set 146 contains a hose cannula 148, which can be connected to an adapter 150 of the insulin pump 116, and also the actual cannula 152 for insertion into a body tissue. As set out above, the filling volume of the entire infusion set 146 or of parts thereof constitutes an essential parameter required for the "priming" by the insulin pump 116. For this purpose, by way of example, on the infusion set 146 itself or on a packaging 154 thereof, which can likewise be regarded as a medical consumable item 122, it is once again possible to provide an optical code 138. This optical code can once again be read in by the insulin pump 116 by means of a code reader 142, such that the insulin pump 116 can utilize these information components concerning the filling volume for a priming process. Other types of information components can also be transmitted in this way. The code reader 142 is arranged symbolically at one end of a housing of the insulin pump 116 in FIG. 2 and can be placed onto the optical code 138 on the packaging 154 and/or the infusion set 146, for example, for the purpose of reading out the information.

Figure 3:
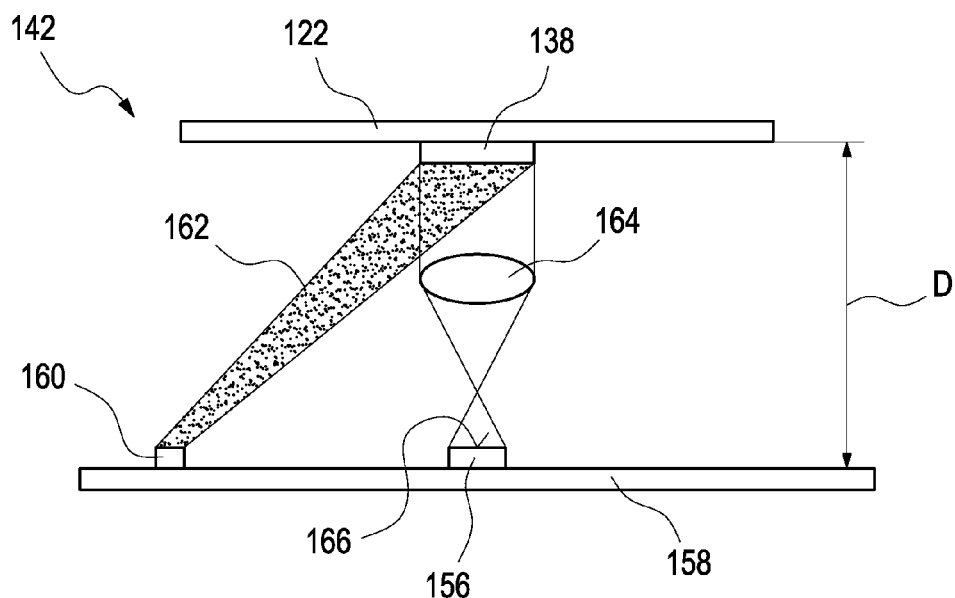
FIG. 3 shows a schematic construction of a conventional barcode reader.

FIG. 3 schematically illustrates an example of a code reader 142 which corresponds to the prior art. The code reader 142 comprises an image sensor 156 having a plurality of individual sensors, which are not illustrated in a resolved fashion in FIG. 3. By way of example, these individual sensors can be arranged in a one-dimensional or two-dimensional fashion. The image sensor can be configured, for example, as an array of photodiodes, as a CCD chip, as a CMOS chip, as an organic photodetector (OPD), or in a similar manner. The image sensor 156 can be arranged, in particular, on a sensor circuit board 158.

Furthermore, the code reader 142 in accordance with the prior art comprises a light source 160, for example one or more light-emitting diodes. This light source 160 serves to illuminate the optical code 138 on the medical consumable item 122 with an illumination light 162. Depending on the type of interaction of said illumination light 162 with the optical code 138, said illumination light can also function as excitation light, where, independently of the type of interaction, both terms are used synonymously in the context of the present invention.

The optical code 138 illuminated in this way is imaged onto an active sensor surface 166 of the image sensor 156 by means of an imaging system 164, which is illustrated symbolically in the form of an individual lens in FIG. 3. This imaging is effected by means of imaging optical elements, such as lenses or lens systems, for example.

In the case of the code readers 142 corresponding to the prior art in accordance with FIG. 3, a considerable distance (designated by D in FIG. 3) is required between the code reader 142 or the electronic circuit board 158 and the medical consumable item 122. This is owing, firstly, to the fact that the illumination light 162 has to impinge laterally on the surface of the optical code 138, wherein said surface has to be illuminated uniformly, and wherein the illumination light 162 must not be impeded by the imaging system 162. Furthermore, the minimum distance, which is generally quite a few millimeters, is concomitantly governed by the imaging system 164 since the latter has to satisfy the optical imaging laws. Moreover, the requirement of the imaging system 164 drives up the costs for the code reader 142 considerably. Overall, therefore, a code reader 142 in accordance with FIG. 3 is beset by some disadvantages in respect of cost aspects and in respect of structural space aspects for portable medical devices 142, for example in accordance with FIG. 1 or 2.

Figure 4:
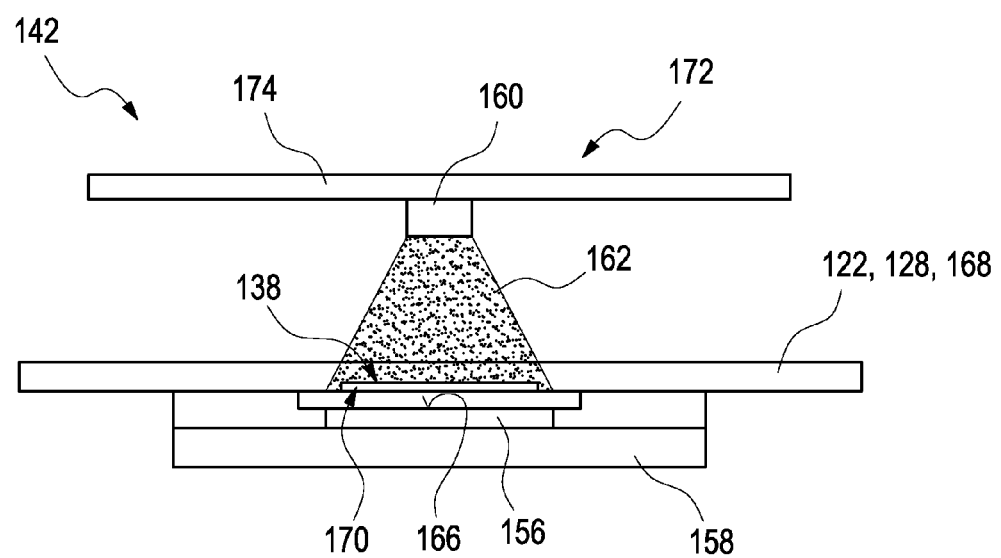
FIG. 4 shows a first exemplary embodiment of a code reader according to the invention with a transmitted-light illumination.

FIG. 4, by contrast, shows a first exemplary embodiment of a code reader 142 according to the invention. In the case of this code reader, a medical consumable item 122 is again used, which, hereinafter and without restricting possible further embodiments, is assumed to be a test strip 128.

In this exemplary embodiment, the test strip 128 comprises a carrier material 168, to which the optical code 138 is applied. In contrast to the exemplary embodiment in accordance with FIG. 3, however, in the case of the configuration according to the invention in accordance with the embodiment of FIG. 4, no imaging system 164 whatsoever is used, rather the optical code 138 is located on a light-optical fiber plate 170 or is positioned directly in front of said fiber plate 170. This light-optical fiber plate 170 in turn is arranged directly above the image sensor 156 or is located on said image sensor 156, although optionally one or a plurality of intermediate layers can also be provided. The image sensor 156 is in turn arranged on a sensor circuit board 158, for example, and can be configured, for example, in the manner described in FIG. 3.

The carrier material 168 of the test strip 128 is wholly or partly produced from a material that is at least partly transparent to the illumination light 162. In this exemplary embodiment, the light source 160, which is a constituent part of an illumination device 172 with an optional illumination circuit board 174, is arranged on the rear side of the test strip 128, that is to say on that side of the test strip 128 which is remote from the optical code 138. The illumination light 162 penetrates through the carrier material 168 and interacts with the optical code 138. This can be effected in various ways. By way of example, the illumination light 162 can be absorbed by the material of the optical code 138, such that a shadow image arises. Alternatively or additionally, however, the material of the optical code 138 can also be configured as luminescent, for example fluorescent, and excite the optical code to emit luminescent light. Once again alternatively or additionally, the illumination light 162 can also interact with the carrier material 168, for example a luminescence converter or dye which is taken up in said carrier material 168 and which generates a secondary illumination light 162, which in turn illuminates the optical code 138 from behind. This last can be used, for example, for making the illumination light 162 more uniform.

In each of the cases illustrated, an image of the optical code arises at the surface of the optical code 138, said image being perceptible. Said image of the optical code 138 is guided to the active sensor surface 166 of the image sensor 156 through the light-optical fiber plate 170.

Figure 5:
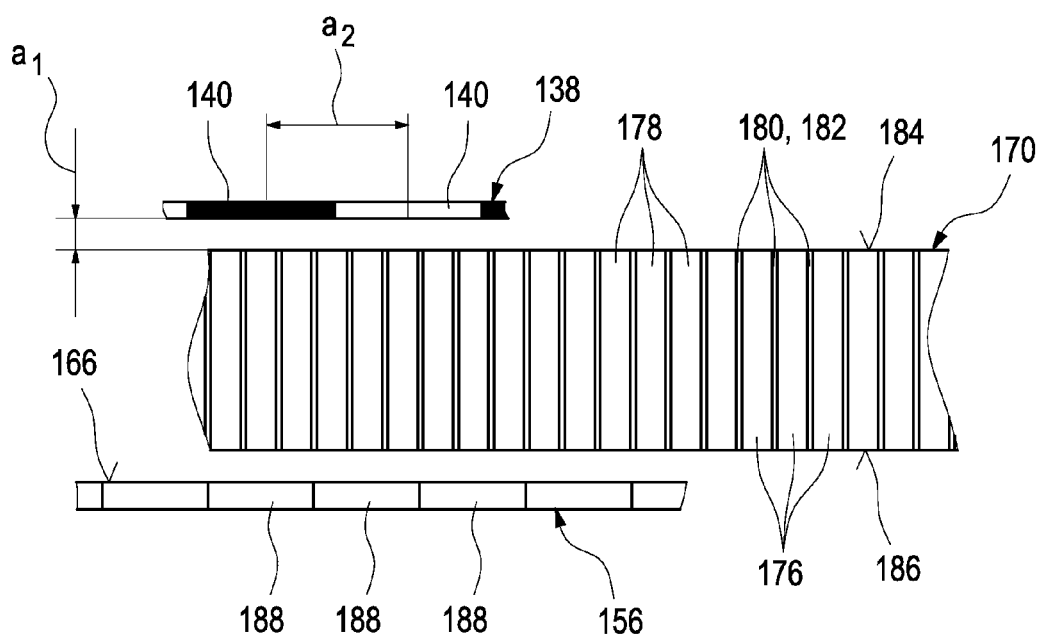
FIGS. 5A and 5B show different detail illustrations of the light-optical fiber plate used in FIG. 4.
Figure 5:
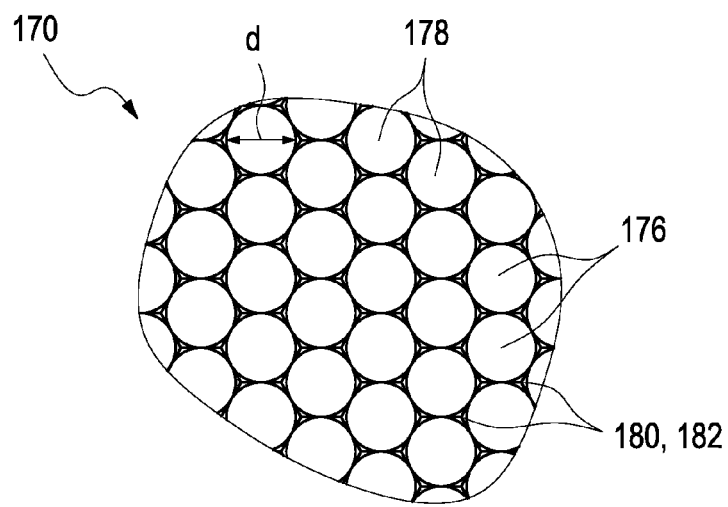

FIGS. 5A and 5B illustrate by way of example, in a sectional illustration from the side and in a partial plan view, respectively, a light-optical fiber plate 170 on the basis of which the construction and the functional principle of such an element are intended to be elucidated. The light-optical fiber plate 170 comprises a multiplicity of optical fibers 176, which may, as can be discerned in FIG. 5B, be arranged with extremely dense packing alongside one another. These optical fibers 176 are fused or adhesively bonded to one another. In this case, the fiber cores 178 can still be completely separated from one another and only be embedded in a common matrix 180. This matrix 180 can be composed, for example, of a cladding (fiber cladding) of the original individual optical fibers 176 in the interspaces between the fiber cores 178.

As can be discerned in FIG. 5A, the optical fibers 176 may be oriented at least substantially parallel to one another, wherein the orientation can be, for example, perpendicular to two surfaces 184, 186 of the light-optical fiber plate. These two surfaces comprise a code-side surface 184 and a sensor-side surface 186.

In contrast to an imaging system based on refraction of light at curved surfaces or at lens systems, the light-optical fiber plate 170 is based on transport of light from the code-side surface 184 to the sensor-side surface 186, or vice versa, by total internal reflection in the optical fibers 176. This means, however, that an article arranged directly in front of the code-side surface 184, for example the image of the optical code 138, is transported virtually through the light-optical fiber plate 170 in a simple manner to the sensor-side surface 186. This can be explained by the fact that a point emitter arranged directly in front of said code-side surface 184 is converted, by the optical fibers 176, into a virtual point emitter situated on the sensor-side surface 186. Since the image of the optical code 138, at least conceptually, can be composed of such point emitters, this means that, if said image is arranged at the code-side surface 184 or directly in front of said code-side surface 184, it is converted virtually into an image on the sensor-side surface 186.

FIG. 5A furthermore illustrates one embodiment of how a spacing between optical code 138 and light-optical fiber plate 170 may be configured. Thus, each optical code 138, as explained with reference to FIG. 1, has modules 140 as smallest optical units. The distance—designated by $a_1$ in FIG. 5A—between the light-optical fiber plate 170 or the code-side surface 184 thereof and the optical code 138 is generally less than a distance—designated by $a_2$ in FIG. 5A—between the midpoints of adjacent modules 140.

Furthermore, FIG. 5A also shows symbolically one embodiment of a relation between the image sensor 156 and the configuration of the light-optical fiber plate 170. The image sensor 156 is composed, as described above, of a plurality of sensors 188, which, as indicated in FIG. 5A, can be arranged for example linearly or in a two-dimensional matrix. The light-optical fiber plate 170 may be configured in such a way that at least three optical fibers 176 of this type are provided per sensor 188 of this type and per dimension. In the case of a two-dimensional arrangement, therefore, in one embodiment there are a minimum number of nine optical fibers 176. A further increase in the number of optical fibers 176 can lead to an improvement in the read-out quality. As explained above, the optical fibers 176 may have a diameter d (see FIG. 5B) of less than 100 μm.

The exemplary embodiment of the code reader 142 in accordance with FIG. 4 requires an arrangement of the illumination device 172 on a rear side of the medical consumable item 122. This can be realized for example when a test strip 128 has been inserted into a blood sugar measuring device 114, since said test strip 128 can be inserted between the illumination device 172 and the sensor circuit board 158. In many cases this arrangement is disadvantageous, however, since the illumination device 172 and the sensor circuit board 158 are usually required to form one unit, for example an individual electronic assembly. This can be realized only with difficulty with the arrangement in accordance with FIG. 4.

FIGS. 6 to 9 correspondingly illustrate embodiments of the code reader 142 which realize such a configuration and in which the illumination of the optical code 138 by the illumination device 172 is substantially effected from the same side of the medical consumable item 122 as the detection by the image sensor 156.

Figure 6:
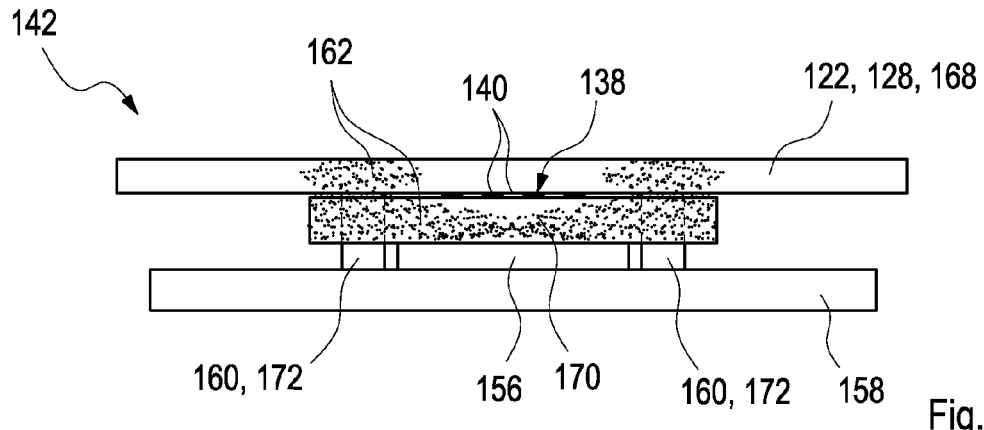
FIG. 6 shows a second exemplary embodiment—alternative to FIG. 4—of a code reader with coupling-in of light into the light-optical fiber plate from the side.

FIG. 6 shows an exemplary embodiment in which once again a light-optical fiber plate 170 bears directly or at only a small distance on the image sensor 156. Laterally with respect to the image sensor 156, light sources 160, for example once again light-emitting diodes, are provided at the edge of the light-optical fiber plate 170 and/or in cutouts thereof. Said light sources 160 radiate illumination light 162 laterally into the light-optical fiber plate 170, that is to say at least approximately perpendicularly to the longitudinal extent of the optical fibers 176 in the light-optical fiber plate 170 and hence to the observation direction of the image sensor 156. By way of example, said illumination light 162 can penetrate through the cladding 182 and/or the matrix 180 of the light-optical fiber plate 170, such that overall the light-optical fiber plate 170 and therefore also the optical code 138 arranged directly thereabove are illuminated. Alternatively or additionally, the illumination light 162 can also penetrate into a carrier material 168 of the medical consumable item 122, which can for example once again be configured as transparent or at least with partly light-scattering properties. Accordingly, a detection of the light reflected by the optical code 138 and/or a transillumination of the optical code 138, that is to say a detection of the transmitted light, can take place. Alternatively or additionally, as explained above, the optical code 138 or the modules 140 thereof can also have optical properties such as luminescence properties, conversion properties or the like. For this purpose, by way of example, a luminescent ink can be applied by printing, a laser conversion of a dye can be effected, or the like. As carrier material 168 having properties that diffusely conduct the illumination light 162, it is possible to use a polyester, for example, which can also be provided with a doping, for example a titanium dioxide ($TiO_2$) doping, such that the carrier material 168 still conveys a white impression, in principle.

In the exemplary embodiment illustrated in FIG. 6, as also in the other configurations according to the invention, one or a plurality of additional elements can also be provided. In particular, one or a plurality of filters can be provided, for example interference filters and/or cut-off filters. Thus, by way of example, between the image sensor 156 and the light-optical fiber plate 170 it is possible to provide a filter in order to separate the illumination light 162 from the actual detection light emerging from the optical code 138. This last is advantageous particularly in the case in which the optical code 138 or the modules 140 thereof or the ink or color used for said modules 140 is or are excited by the illumination light 162 to emit detection light, which differs spectrally from the illumination light 162. The contrast and the signal-to-noise ratio of the signal recorded by the image sensor 156 can be considerably improved in this way.

Figure 7:
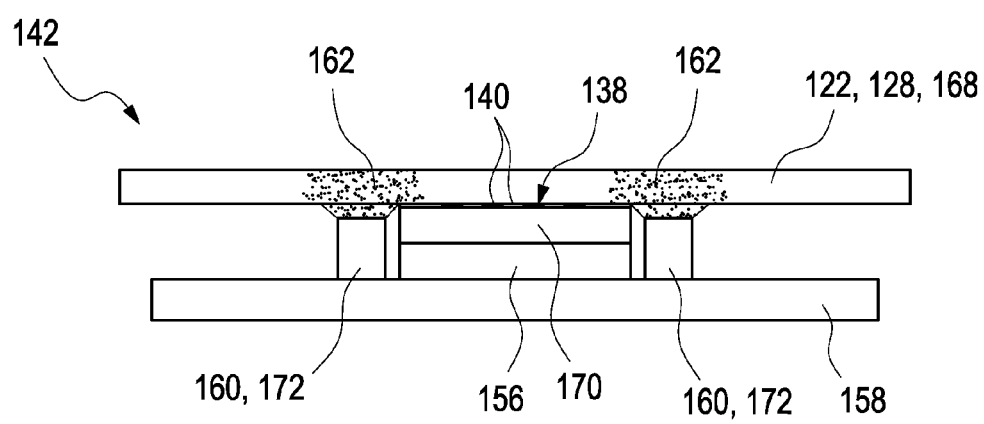
FIG. 7 shows an exemplary embodiment of the code reader with coupling-in of light into a test strip in the case of an absorbent optical code.

An exemplary embodiment of the code reader 142 that is similar, in principle, to FIG. 6 is illustrated in FIG. 7. Once again the light sources 160 are arranged laterally alongside the light-optical fiber plate 170. In contrast to the exemplary embodiment in accordance with FIG. 6, however, in this exemplary embodiment there is substantially no coupling of illumination light 162 into the light-optical fiber plate 170 from the side, which can be realized, for example, by means of a geometrical orientation and/or directionality of these light sources 160 and/or by corresponding shielding elements, for example light-opaque coloration of the side edges of the light-optical fiber plate 170, for example by means of a blackening.

In this case, the illumination light 162 is scattered in the carrier material 168 of the medical consumable item 122, for which purpose said carrier material can once again be configured accordingly. This scattering can be effected with an unchanged wavelength, or it is possible to provide scattering centers having wavelength-converting properties. By way of example, titanium dioxide ($TiO_2$) particles can again be provided in the carrier material 168, which, by way of example, can comprise a transparent plastic, for example once again a polyester, e.g. Melinex. On account of the scattering properties of said scattering centers, an inhomogeneous intensity distribution arises in the matrix material of the carrier material 168. The optical code 138 is illuminated from behind in this way, which produces a required contrast between, for example, black and white modules 140 of said optical code 138. As an alternative or in addition to this absorptive detection, however, an excitation of the optical code 138 by the illumination light 162 can also once again be effected, for example once again an excitation to luminescence. As an alternative or in addition to the absorptive image recording, this spectrally changed detection light can also be recorded, for example by means of a spectral separation in the image sensor 156.

Figure 8:
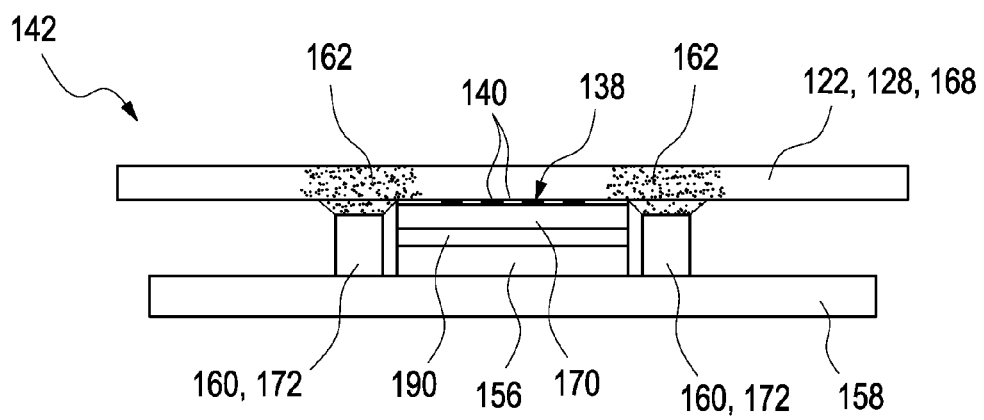
FIG. 8 shows an exemplary embodiment of a code reader with coupling-in of light into a test strip in the case of an fluorescent optical code.
Figure 9:
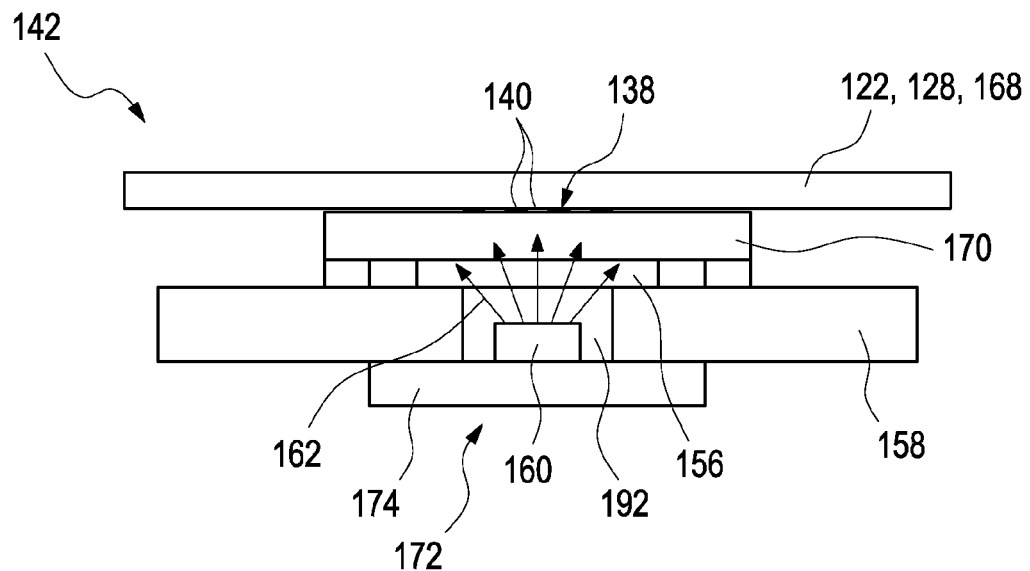
FIGS. 9A and 9B show exemplary embodiments of a code reader with coupling-in of light through an image sensor.
Figure 9:
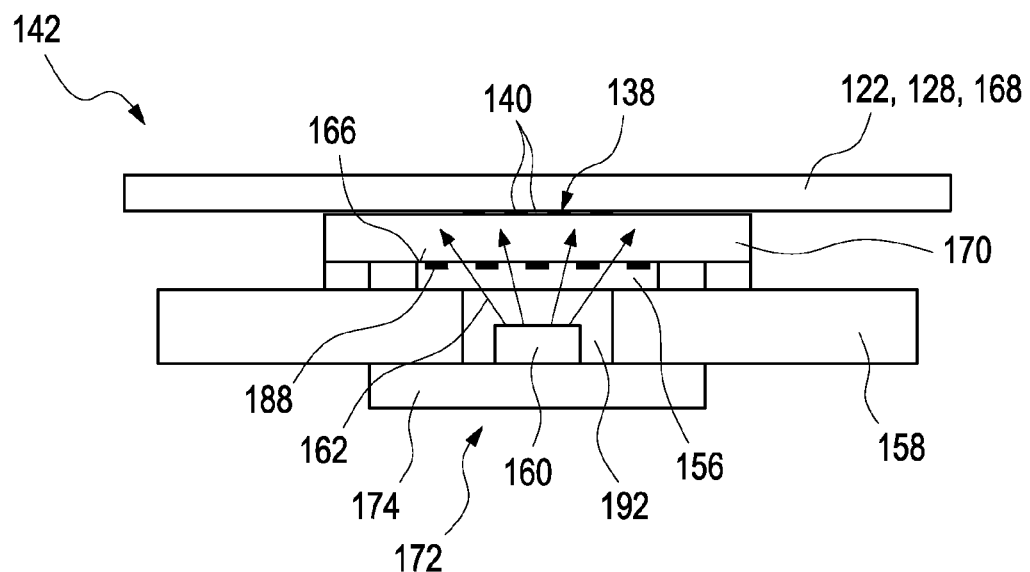

FIG. 8 illustrates a further exemplary embodiment of a code reader 142, which is once again similar to the exemplary embodiment in accordance with FIG. 7 in terms of the construction, such that reference may largely be made to the description of FIG. 7. In this embodiment, too, there is once again no coupling of illumination light 162 laterally into the light-optical fiber plate 170, rather there is exclusively coupling of light into a carrier material 168 of the medical consumable item 122.

The exemplary embodiment shown in FIG. 8 has advantages over the exemplary embodiment in accordance with FIG. 7 with regard to suppression of background light. For this purpose, illumination light 162 is used which is changed spectrally in terms of its properties by the optical code 138 or the modules 140 thereof or an ink or color used for said modules. By way of example, short-wave light can be used, which constitutes an excitation light. By means of this excitation light 162, luminescence can be excited in the color or ink of the optical code 138, for example. This luminescent light, which has a shorter wavelength than the excitation light 162 on account of a Stokes shift, for example, can be separated from the excitation light 162 by means of suitable spectrally selective elements. By way of example, for this purpose, in the case of the construction in accordance with FIG. 8, a filter 190 is provided between the light-optical fiber plate and the image sensor 156, which filter, although it is at least substantially transmissive to detection light, at least substantially suppresses the excitation light 162. Said filter 190 can be provided, for example, directly between the light-optical fiber plate 170 and the image sensor 156. Alternatively or additionally, however, other arrangements are also possible. In order to prevent the image quality on the image sensor 156 from being impaired by the thickness of the filter 190, the filter 190 comprises thicknesses of only a few hundred μm or less. By way of example, a filter coating can be provided directly on the image sensor 156 or the active sensor surface 166 thereof. Alternatively or additionally, the image sensor 156 itself or the sensors 188 thereof themselves can also be equipped with spectrally selective properties, for example with a spectral sensitivity only in the range of the detection light to be detected.

One advantage of the use of fluorescent ink for the optical code 138 furthermore also consists in the fact that the optical code can be made at least substantially invisible to a user. Consequently, the optical code 138 can also be used for protection against counterfeiting since it is not directly discernable to a user or possible counterfeiter of the medical consumable item 122.

FIG. 9A schematically illustrates a further exemplary embodiment of a code reader 142, which follows a third illumination concept that can be realized as an alternative or in addition. While rear-side transillumination is effected in FIG. 4 and while lateral illumination is effected in FIGS. 6 to 8, the exemplary embodiment in accordance with FIG. 9A involves effecting illumination with illumination light 162 directly through the light-optical fiber plate 170, wherein the illumination is effected substantially parallel to the longitudinal extent of the optical fibers 176. In the exemplary embodiment illustrated, this is realized by virtue of the fact that the image sensor 156 is configured as at least substantially transparent to the illumination light 162. By way of example, this can be effected by virtue of the image sensor 156 or the sensors 188 thereof having a semiconductor material having a band gap. The illumination light 162 can be chosen in such a way that it has a longer wavelength than the wavelength corresponding to said band gap, such that only negligible absorption of the illumination light 162 in the image sensor 156 takes place. Light-converting materials can then be provided in the carrier material 168 and/or in the material of the optical code 138, said light-converting materials converting this long-wave illumination light 162 into correspondingly shorter-wave detection light, which can then once again be perceived by the image sensor 156.

As an alternative or in addition to the embodiment described in FIG. 9B, in which the illumination light 162 penetrates directly through the material of the image sensor 156, the image sensor 156 can also comprise regions specifically configured for passage of light. This is illustrated by way of example in FIG. 9B, which largely corresponds to FIG. 9A, such that, for the description of the construction, reference may largely be made to the above description of FIG. 9A.

Thus, the light-transmissive regions in the image sensor 156 can be configured in various ways. By way of example, these regions can be realized by corresponding openings in the image sensor 156, through which the illumination light 162 can penetrate. Alternatively or additionally, as illustrated in the exemplary embodiment in accordance with FIG. 9B, it is also possible to provide uncoated regions in the image sensor 156, through which the passage of light can take place. This last can be realized, for example, by means of an array of sensors 188 which are arranged in a manner spaced apart from one another on a transparent carrier, for example a glass plate. Through the interspaces between the individual sensors 188, excitation light 162 can then pass in a manner at least substantially unimpeded. Various other configurations are possible. The illumination light 162 can then once again interact with the optical code 138 in various ways. By way of example, reflection, absorption, luminescence excitation or the like can again be mentioned here.

With regard to the interspaces between the individual sensors 188 it can be mooted that these are present anyway in many image sensors 156. The ratio between that proportion of an active sensor surface 166 which is formed by the sensors 188 and the total active sensor surface 166 is generally referred to as the filling factor. Owing to structural dictates, this filling factor has values of less than 100% in most image sensors 156. In the context of the present invention, not only can this be afforded tolerance, but it can even be deliberately exploited. Thus, by way of example, at least one portion of electronics can already be arranged in the interspaces between the sensors 188. By way of example, this can be a portion of the electronics required for the evaluation of the signals of the sensors 188, for example transistor electronics, amplifiers, diodes or combinations of the abovementioned and/or other elements. These electronics can also be configured as at least partly transparent. In this case, therefore, at least one portion of the electronics can already be arranged on and/or directly below the active sensor surface 166, for example in the same layer plane in which the sensors 188 are also arranged. As a result, by way of example, once again the entire structural size of the image sensor 156 can be reduced, and it is possible to use more cost-effective image sensors 156, for example semiconductor image sensors. By way of example, it is possible to use image sensors 156 having filling factors of approximately 25%. The disadvantages of low filling factors, residing in a lower luminous efficiency, in particular, do not become apparent to the same extent in image sensors 156 as in camera systems, for example. In this respect, comparatively low filling factors can also be afforded tolerance. Generally, by way of example, as described above, CMOS structures can be used as image sensors 156.

In the case of the arrangements in accordance with FIG. 9A or 9B, by way of example, the sensor circuit board 158 can be equipped with an opening 192, into which one or a plurality of light sources 160 of the illumination device 172 project. Other configurations in which the at least one light source 160 or a light source of this type are or is arranged behind the image sensors 156 are also possible.

In certain embodiments of the present invention, the complete image of the optical code 138 may be imaged onto the active sensor surface 166. For this purpose, by way of example, the active sensor surface 166 can be equipped with a suitable size. Alternatively or additionally, however, it is also possible, in principle, to configure the light-optical fiber plate 170 with demagnifying or magnifying properties. For a demagnification of an image, by way of example, it is possible to alter the density of the optical fibers 176 on the sensor-side surface 186 of the light-optical fiber plate 170 by comparison with the code-side surface 184, for example make it lower than on the code-side surface 184, overall the number of optical fibers 176 generally remaining the same. In principle, such a magnifying or in the same way demagnifying configuration of the light-optical fiber plate 170 is also conceivable for applications other than the applications described in the context of the present invention. In this way, however, in the context of the present invention, the area of the optical code 138 can be adapted, for example, to the size of the light-optical fiber plate 170, such that the latter is utilized optimally, for example, and the structural size and costs therefore remain small and low, respectively.

Figure 10:
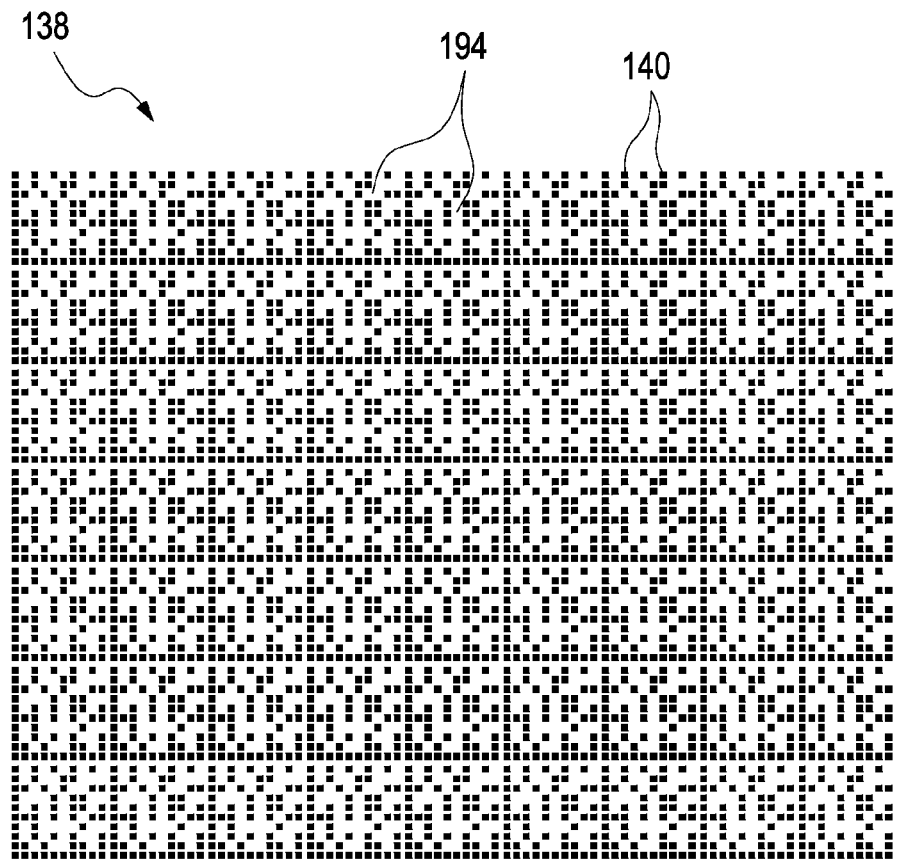
FIG. 10 shows an exemplary embodiment of a redundant optical code.

Alternatively, however, it is also possible to detect only a part of the optical code 138 by means of the image sensor 156. In such embodiments, the optical code 138 may be configured with redundant information. One example of such a configuration is illustrated in FIG. 10. In this exemplary embodiment, the optical code 138 has repeating, identical code units 194. These code units 194 are in each case configured with the same pattern of modules 140 which can be detected. In this way, even if the image sensor 156 only detects an excerpt from the optical code 138, such as an excerpt which comprises at least one complete code unit 194, it is possible to read out the information contained in this optical code 138.

Generally, the evaluation of the information contained in the optical code 138, independently of the configuration of the optical code 138, can also be effected wholly or partly in the code reader 142. For this purpose, by way of example, the image sensor 156 can be equipped with its own intelligence which already enables a partial or complete evaluation of the optical code 138. By way of example, filters, image recognition algorithms or the like can already be implemented in the image sensor 156. A more extensive evaluation is also possible, in principle. Alternatively or additionally, the code reader 142 can also comprise additional electronic components which furthermore completely or partly realize the evaluation of the optical code 138 in order to obtain the at least one information component contained therein. These additional components can, for example, likewise be arranged on the sensor circuit board 158 or can also be arranged separately. Once again alternatively or additionally, a further evaluation can also be performed by a control unit of the medical device 112, for example a central control unit of a blood sugar measuring device 114 or an insulin pump 116. Various configurations are possible.

In the above exemplary embodiments, the illumination of the optical code 138 by means of the illumination device 172 has always been considered to be static. This is not necessarily the case, however, rather, alternatively or additionally, a temporally resolved illumination and/or measurement can also be effected. One exemplary embodiment of such a dynamic or temporally resolved measurement scheme is shown symbolically in FIG. 11. Numerous further measurement schemes are possible.

Figure 11:
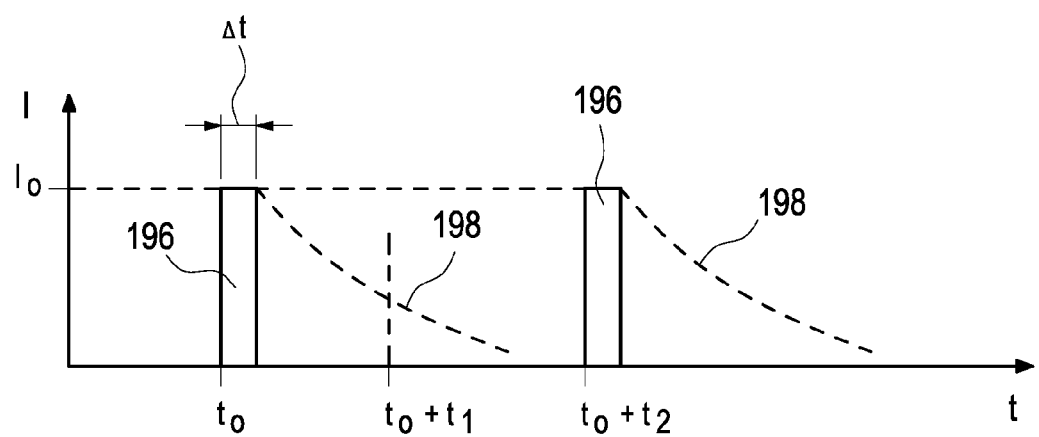
FIG. 11 shows an exemplary embodiment of a possible temporally resolved measurement scheme.

In FIG. 11, an intensity I of the illumination light 162 is plotted against the time t. It can be discerned from this that an illumination pulse 196 with an intensity $I_0$ is emitted at an instant $t_0$. Said illumination pulse 196, as indicated in a dashed fashion in FIG. 11, can, for example, excite a dye of the optical code 138 to persistence 198 that lasts longer than the actual time duration $\Delta t$ of the illumination pulse 196. By way of example, said persistence 198 can comprise a luminescence or more specifically here a phosphorescence.

At an instant $t_0+t_1$, where $t_1$ is greater than $\Delta t$, it is then possible to effect an interrogation of the detection light in the form of the persistence 198 by means of the image sensor 156. This can be effected, for example, by means of a corresponding "gate" in an electronic driving of the image sensor, which is triggered by the illumination pulse 196. This image recording, too, can, although not illustrated in FIG. 11, once again be effected over a certain time duration, such that a sufficient amount of detection light can be recorded by the image sensor 156. In this way, by means of the temporal measurement scheme shown in FIG. 11, by means of an excitation-response measurement method, the illumination light 162 can be separated from the detection light in the form of the persistence 198, as a result of which a great improvement in the signal-to-noise ratio and background suppression can be obtained.

The measurement method can also be carried out repeatedly, which is likewise indicated in FIG. 11. Thus, at an instant $t_2$, which is greater than $t_1$, the illumination pulse 196 can be repeated, for example periodically. In this way, the measurement scheme can be carried out periodically, for example, such that it is also possible to realize a frequency-selective evaluation by means of a lock-in method.

Figure 12:
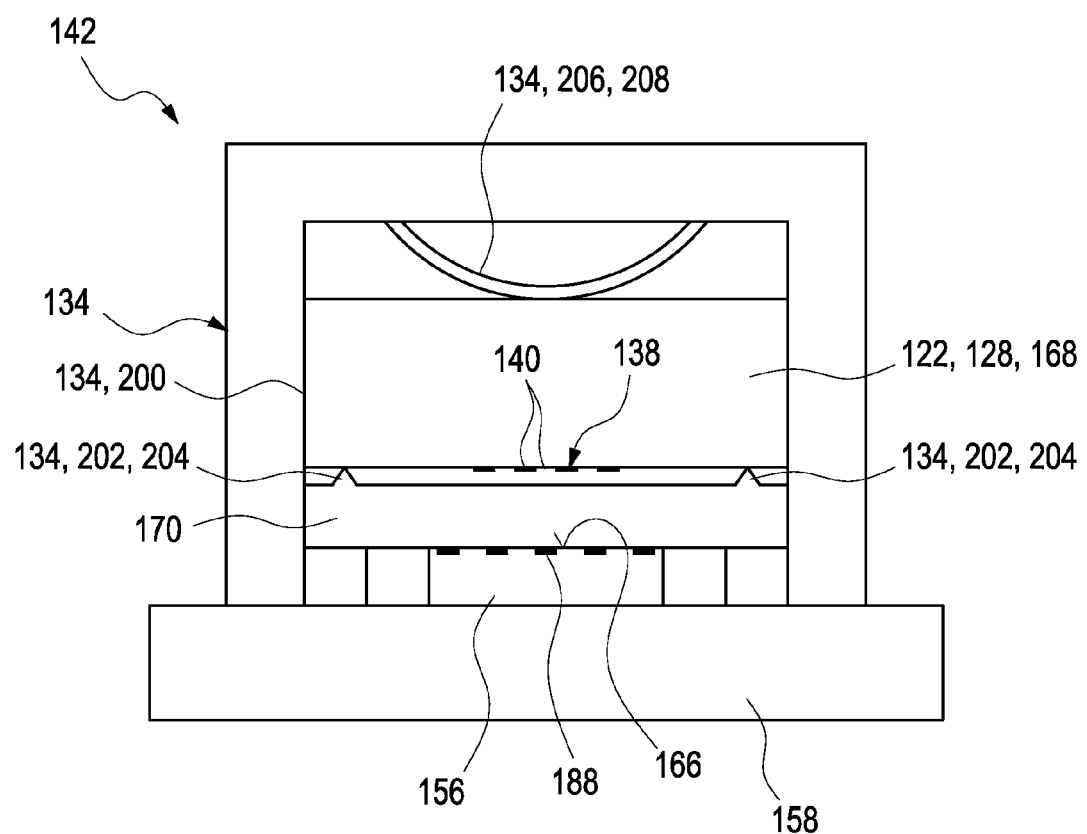
FIG. 12 shows an exemplary embodiment of a code reader with a positioning device.

FIG. 12 illustrates an exemplary embodiment of a code reader 142 which is an alternative to FIGS. 4, 6 to 8 and 9A and 9B and which shows an example of a possible positioning device 134 in a schematic illustration. In this case, the code reader 142 can be configured, for example, substantially like the code reader 142 described in the previous exemplary embodiments, such that, for possible embodiments, reference may be made to the above description, for example. An illumination device 172 is not illustrated in FIG. 12. The illumination can likewise be effected, for example, once again as in the exemplary embodiments described above.

In this case, the positioning device 134 optionally comprises an insert 200 in the exemplary embodiment illustrated in FIG. 12, into which insert the medical consumable item 122 can be inserted. By way of example, this medical consumable item 122 can once again be a test element 124, for example a test strip 128. However, other types of medical consumable items 122 are also again possible, wherein the positioning device 134 can be adapted to the geometrical shape of said consumable items 122. Thus, by way of example, the insert 200 can be replaced by corresponding other types of mounts or similar devices.

In the exemplary embodiment illustrated in FIG. 12, the positioning device 134 furthermore optionally comprises a spacer 202. This spacer 202 comprises, for example, a spacer rail 204 designed to ensure a predetermined minimum distance between the medical consumable item 122 and the light-optical fiber plate 170. In this way it is possible to ensure that the light-optical fiber plate 170 is not damaged, worn or contaminated by the medical consumable item 122, in particular during the insertion and/or withdrawal thereof. By way of example, the minimum distance can at least substantially correspond to the distance designated by $a_1$ in FIG. 5A.

Furthermore, the positioning device 134 in the exemplary embodiment illustrated in FIG. 12 optionally comprises a press-on element 206, which is indicated here for example as a spring element 208. Said press-on element 206 applies to the medical consumable item 122 a force in the direction of the light-optical fiber plate 170. In this way, the medical consumable item 122 is pressed against the spacer rail 204, thus ensuring that the distance between the medical consumable item 122 and the light-optical fiber plate 170 does not exceed a desired maximum distance. By way of example, the positioning device 134 can be designed to hold the medical consumable item 122 at the above-described distance $a_1$. However, other configurations of the positioning device are also possible, in principle.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A medical system comprising:
    at least one handheld medical device configured to perform at least one medical function; and
    at least one medical consumable item having at least one two-dimensional optical code provided thereon,
    wherein the medical device is configured to interact with the medical consumable item to perform the medical function, the medical device comprising:
    at least one code reader configured to read at least one information component from the optical code of the medical consumable item when the medical consumable item is in a read position relative to the medical device, the code reader comprising:
    at least one image sensor having a plurality of sensors,
    at least one planar light-optical fiber plate having first and second planes,
    the plate being generally configured to transport light from the first plane to the second plane, the plate further being generally configured to guide an image of the optical code to the image sensor without appreciably altering the image during transport, the optical code comprising a plurality of optically readable modules each comprising a smallest information unit,
    wherein the light-optical fiber plate comprises a plurality of substantially parallel oriented optical fibers arranged perpendicular to the first plane and the second plane, and
    at least one illumination device configured to illuminate the optical code on a side of the optical code generally facing the image sensor,
    wherein the medical consumable item and the medical device being positioned relative to each other in the read position such that a first distance between the plate at the first plane and the optical code is less than a second distance between the midpoints of adjacent modules of the optical code, wherein the illumination device comprises at least one light source and is configured to illuminate the optical code on one side, from the same side on which the image sensor also is provided, in one or more of the manners of (a) through the plate, (b) from a side of the optical code substantially perpendicular to a viewing direction of the plate through a carrier material of the medical consumable item, and (c) through the image sensor onto the medical consumable item in a region of the optical code, and wherein the medical function is performed on a patient sample or influences a patient body state.

2. The medical system of claim 1, wherein the plurality of optical fibers have a diameter of less than 100 micrometers.

3. The medical system of claim 1, wherein the illumination device comprises at least one light source which is configured to trans-illuminate the medical consumable item in the region of the optical code.

4. The medical system of claim 1, wherein the illumination device is configured to illuminate the medical consumable item sequentially with light having different wavelengths.

5. The medical system of claim 1, wherein the code reader is configured to record the image of the optical code in a time-delayed manner with respect to an illumination by the illumination device.

6. The medical system of claim 1, wherein the medical device comprises at least one of the following devices:
   an analysis device for detecting at least one metabolite in the body fluid, wherein the analysis device is designed to interact with the medical consumable item in the form of at least one test element for detecting the metabolite;
   a metering device comprising an insulin pump, wherein the metering device is designed to interact with the consumable item in the form of a catheter and/or a cannula, wherein the information comprises information about a filling volume of the catheter and/or of the cannula.

7. The medical system of claim 1, wherein the image sensor has at least two regions having a differing spectral sensitivity.

8. The medical system of claim 1, furthermore comprising a positioning device, which is designed to position the medical device and the consumable item relative to one another.

9. The medical system of claim 1, wherein the light-optical fiber plate is dimensioned in such a way that at least three optical fibers are provided per dimension of the optical code per optically readable module.

10. The medical system of claim 1, wherein the medical consumable item comprises a carrier material in the region of the optical code, wherein the carrier material comprises a transparent plastic having transparent or light-scattering properties.

11. The medical system of claim 10, wherein the carrier material comprises a transparent polyester.

12. The medical system of claim 10, wherein the transparent plastic is doped with $TiO_2$ in such a way that a substantially white overall impression of the carrier material arises, wherein the carrier material has diffusely light-conducting properties.

13. The medical system of claim 1, wherein the optical code is designed to interact differently with light having different wavelengths.

14. The medical system of claim 1, wherein the optical code has at least partly luminescent properties, and further wherein the modules of the optical code comprise at least one light converter configured to convert an excitation light into a light having a different wavelength than the excitation light.

15. The medical system of claim 14, wherein the at least one light converter comprises a phosphor.

16. The medical system of claim 14, wherein the at least one light converter converts the excitation light into a light having a longer wavelength than the excitation light.

17. The medical system of claim 1, wherein the medical consumable item comprises a carrier having a carrier material in the region of the optical code, wherein the carrier furthermore comprises at least one light converter, wherein the light converter is designed to convert an excitation light into a light having a different wavelength than the excitation light.

18. The medical system of claim 1, wherein the image sensor and the light-optical fiber plate form one unit having a joint thickness of less than 5 mm.

19. The medical system of claim 1, wherein the image sensor does not include lens systems.

* * * * *